(12) United States Patent
Rubenstein et al.

(10) Patent No.: US 11,548,001 B1
(45) Date of Patent: Jan. 10, 2023

(54) AIR TO LIQUID MICRO-FLUIDIC CHAMBER

(71) Applicant: Government of the United States, as represented by the Secretary of the Air Force, Wright-Patterson AFB, OH (US)

(72) Inventors: Mitchell Rubenstein, Beavercreek, OH (US); Douglas Adkins, Albuquerque, NM (US); Patrick Lewis, Albuquerque, NM (US); John Rogers, Wilmette, IL (US); Sungbong Kim, Champaign, IL (US); Steve Kim, Dayton, OH (US); Michael Brothers, Lebanon, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 0 days.

(21) Appl. No.: 16/379,890

(22) Filed: Apr. 10, 2019

Related U.S. Application Data

(60) Provisional application No. 62/655,478, filed on Apr. 10, 2018.

(51) Int. Cl.
| | |
|---|---|
| C12M 1/40 | (2006.01) |
| B01L 3/00 | (2006.01) |
| C12M 3/06 | (2006.01) |
| F16K 99/00 | (2006.01) |

(52) U.S. Cl.
CPC ....... *B01L 3/502738* (2013.01); *C12M 23/16* (2013.01); *F16K 99/0001* (2013.01)

(58) Field of Classification Search
CPC ............... C12M 23/16; F16K 99/0001; C12Q 2565/629; B01L 9/527; B01L 3/5027; B01L 3/502753; B01L 3/502738; B01L 5/00; B01L 5/02; B81B 2201/06; B01B 2201/05; B01B 2201/058; G01N 33/0024; G01N 33/0019; G01N 33/0004; G01N 2021/7786; C12N 9/18; C12N 9/008; C12N 9/0065; C12Y 301/01007; C12Y 114/99001; C12Y 111/01007
See application file for complete search history.

(56) References Cited

U.S. PATENT DOCUMENTS

| | | | |
|---|---|---|---|
| 5,858,457 A | 1/1999 | Brinker et al. | |
| 2005/0095698 A1* | 5/2005 | Carlson | G01N 21/6445 435/287.2 |
| 2007/0116607 A1* | 5/2007 | Wang | B01L 3/502715 422/83 |
| 2010/0144059 A1* | 6/2010 | Frisk | G01N 29/022 436/518 |

OTHER PUBLICATIONS

Byunghoon Bae et al. "A Fully-IntegratedMEMS Preconcentrator for Rapid Gas Sampling" Transducers 2007—2007 International Solid-State Sensors, Actuators and Microsystems Conference, Jun. 10-14, 2007, Date Added to IEEE Xplore: Sep. 24, 2007, 4pgs (Year: 2007).*
Wang et al. "Quantitative determination of trace hydrogen peroxide in the presence of sulfide using the Amplex Red/horseradish peroxidase assay" Analytics Chimica Acts 963 (2017) 61-67 (Year: 2017).*
Li et al. "Improved measurements of scant hydrogen peroxide enable experiments that define its threshold of toxicity for *Escherichia coli*" FreeRadicalBiologyandMedicine120(2018)217-227 (Year: 2018).*
Čolović, M., et al., "Acetylcholinesterase Inhibitors: Pharmacology and Toxicology," Current Neuropharmacology, 2013, vol. 11, No. 3, pp. 315-335.
Santillo, M., et al., "A fluorescence assay for measuring acetylcholinesterase activity in rat blood and a human neuroblastoma cell line (SH-SY5Y)," Journal of Pharmacological and Toxicological Methods, 76, 2015, pp. 15-22.
Meller, K., et al., "Microfluidic reactors with immobilized enzymes—Characterization, dividing, perspectives," Sensors and Actuators B 244, 2017, pp. 84-106.
Yotter, R., et al., "A review of photodetectors for sensing light-emitting reporters in biological systems," IEEE Sensors Journal, vol. 3, No. 3, Jun. 2003, pp. 288-303.
Nakajima, H., et al., "Photochemical immobilization of protein on the inner wall of a microchannel and Its application in a glucose sensor," Analytica Chimica Acta 562, 2006, pp. 103-109.
Wu, X., et al., "The surface-enhanced Raman spectra of aflatoxins: spectral analysis, density functional theory calculation, detection and differentiation," Analyst, 2012, 137, pp. 4226-4234.
Yu, H., et al., "Low temperature and deformation-free bonding of PMMA microfluidic devices with stable hydrophilicity via oxygen plasma treatment and PVA coating," RSC Adv., 2015, 5, pp. 8377-8388.
Skene, W., et al., "Vapor Pressure of Tri-n-butyl Phosphate," Journal of Chemical and Engineering Data, vol. 40, No. 2, pp. 394-397.

(Continued)

*Primary Examiner* — Thane Underdahl
(74) *Attorney, Agent, or Firm* — AFMCLO/JAZ; Chastity D. S. Whitaker

(57) ABSTRACT

A system, apparatus, and method include a pump to deliver vapor including airborne contaminants including organic compounds including a target analyte; a collector to transfer the airborne contaminants by autonomous liquid extraction into a mobile organic liquid phase; a micro-fluidic chamber including immobilized biorecognition elements that bind to analytes delivered from the mobile organic liquid phase; a mechanism to introduce the mobile organic liquid phase to a buffer containing a plurality of substrates causing a series of biochemical reactions that create a change corresponding to a concentration of the target analyte; and a detector to perform real-time analysis that correlates to a concentration of the organic compounds to determine a presence of the target analyte.

9 Claims, 28 Drawing Sheets

(56) References Cited

OTHER PUBLICATIONS

Bae, B., et al., "A Fully-Integrated MEMS Preconcentrator for Rapid Gas Sampling," U.S. Air Force Report AFRL-PR-WP-TP-2007-224 for submission of a Conference paper submitted to the Proceedings of the Transducers 2007 Conference, Mar. 19, 2007, pp. 1-4.
Andreescu, S., et al., "Screen-printed electrode based on AChE for the detection of pesticides in presence of organic solvents," Talanta 57, 2002, pp. 169-176.
Mionetto, N., et al., "Acetylcholinesterase in organic solvents for the detection of pesticides: Biosensor application," Biosensors and Bioelectronics, vol. 9, Issue 6, 1994, pp. 463-470.
Soares, C., et al., "Protein structure and dynamics in ionic liquids. Insights from molecular dynamics simulation studies," Biophysical Journal, vol. 84, Mar. 2003, pp. 1628-1641.
Cernosek, R., et al., "Micro-analytical systems for national security applications," Proceedings of SPIE, vol. 6223, Micro (MEMS) and Nanotechnologies for Space Applications, May 18, 2006, p. 622306-1 to 622306-13.

\* cited by examiner

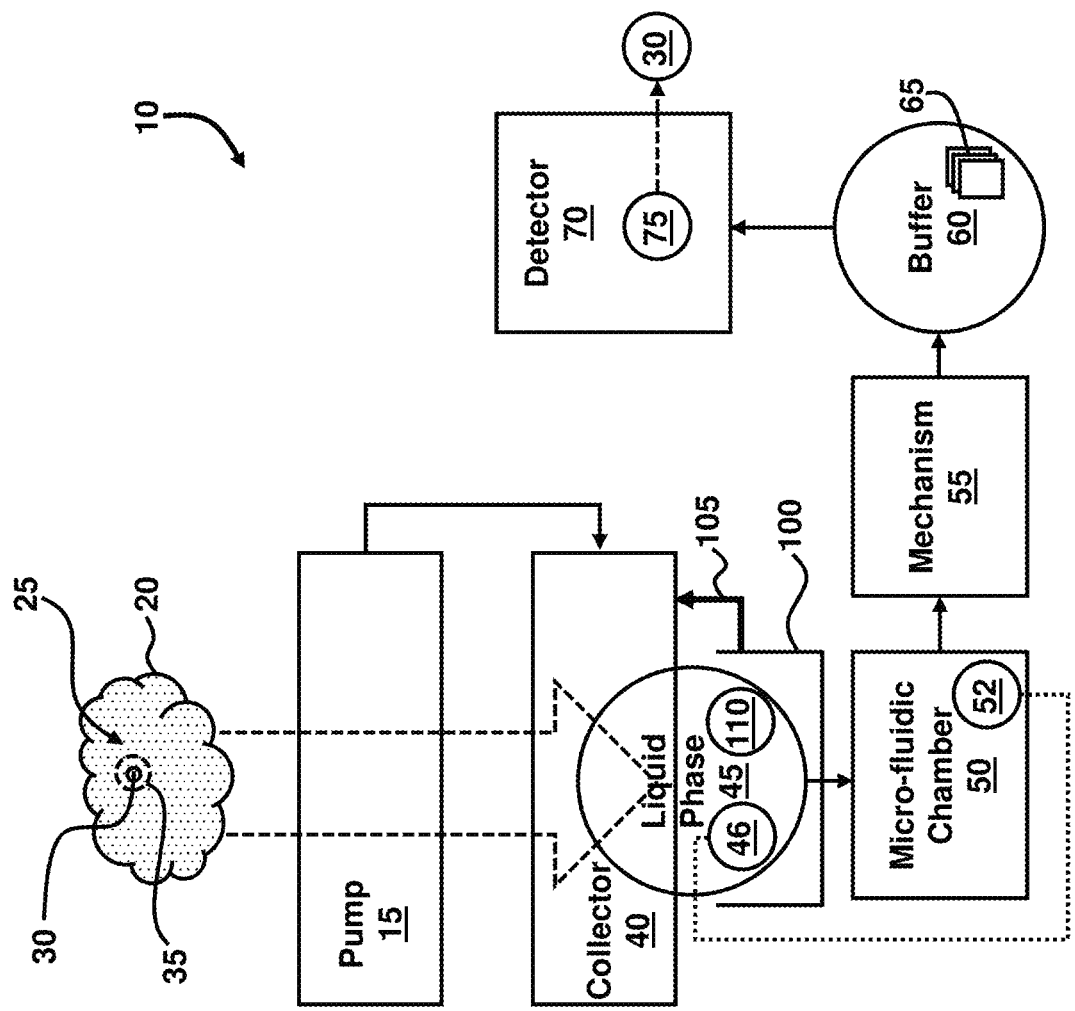

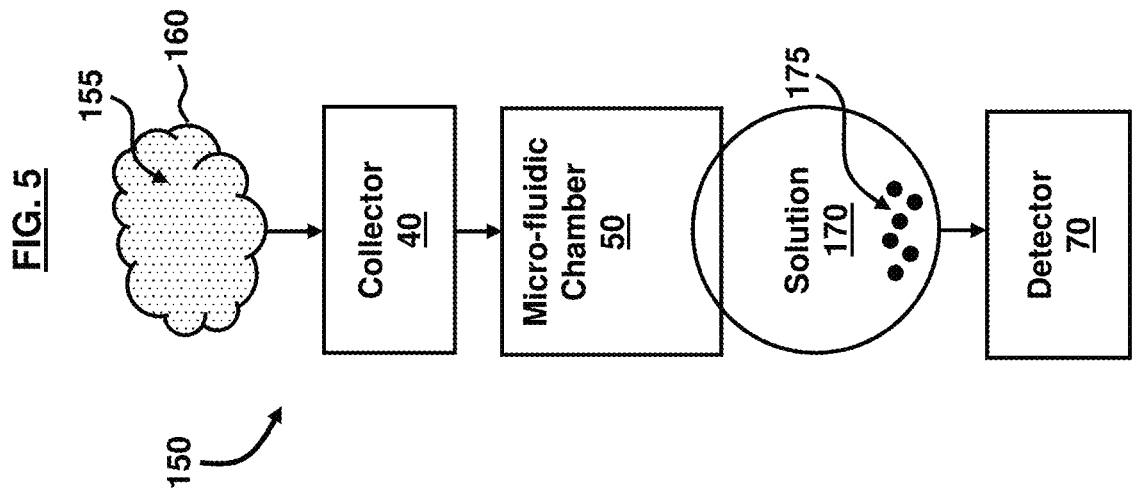

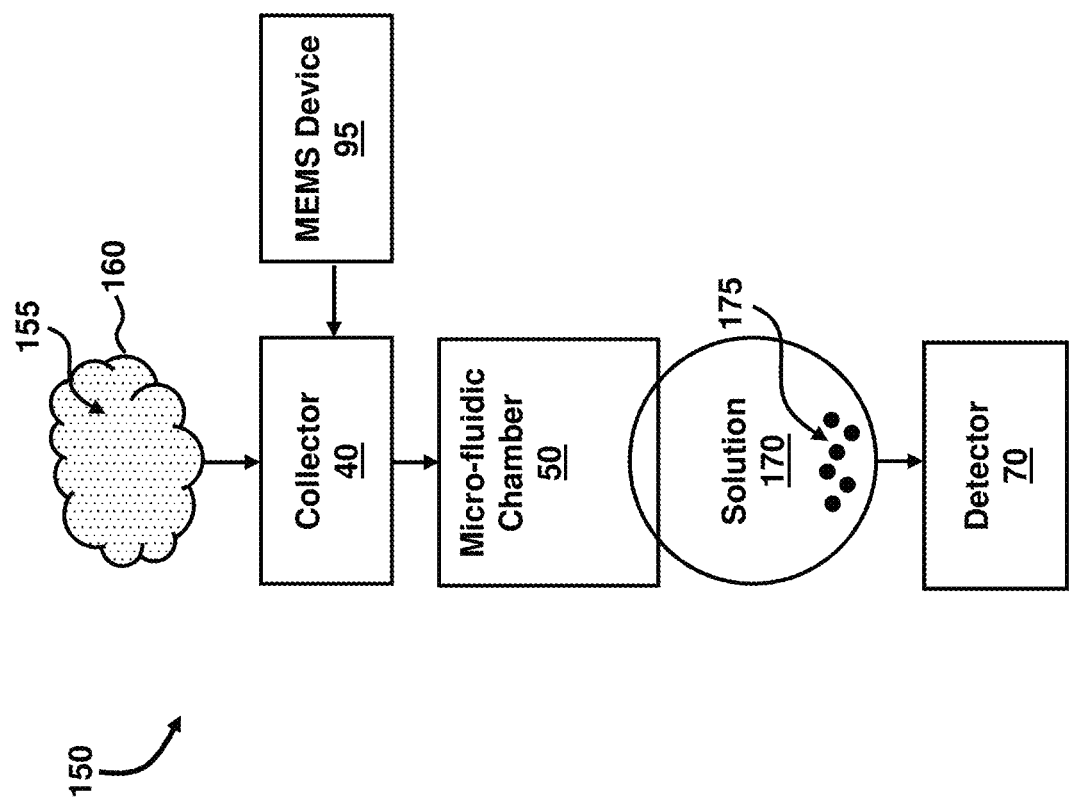

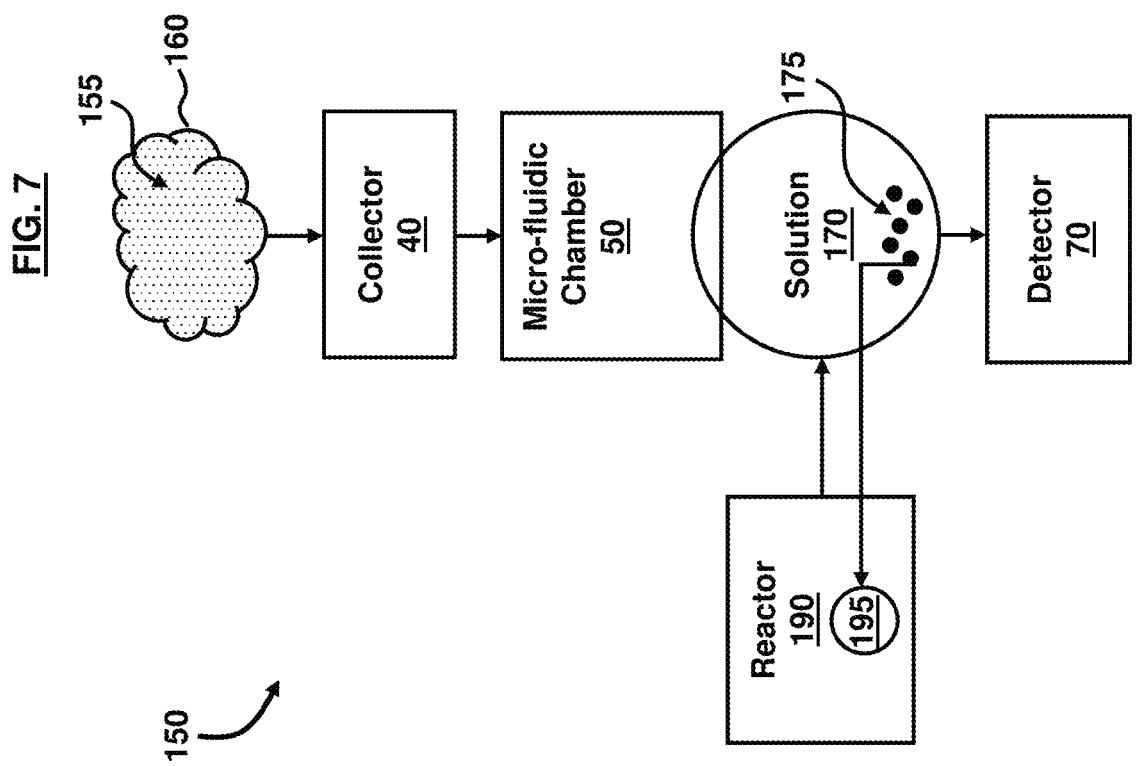

Oxidizing the hydrogen peroxide by a peroxidase — 335

Exciting the fluorophore to fluorescence — 340

Correlating the fluorescence to an inverse correlation of a concentration of organo-phosphates — 345

AIR TO LIQUID MICRO-FLUIDIC CHAMBER

CROSS-REFERENCE TO RELATED APPLICATION(S)

This application claims the benefit of U.S. Provisional Patent Application No. 62/655,478 filed on Apr. 10, 2018, which is hereby incorporated herein by reference in its entirety.

GOVERNMENT INTEREST

The invention described herein may be manufactured and used by or for the Government of the United States for all government purposes without the payment of any royalty.

BACKGROUND

Field of the Invention

The embodiments herein generally relate to contaminant detectors, and more particularly to detectors of organo-phosphate compounds, opioids, cannabinoids, and other classes of organic compounds.

Background of the Invention

There is a gap in surveillance in military and civilian operations. For example, there is concern with the air quality in aircraft for exposure to organo-phosphates that are found in fluids used by aircraft; specifically, tri-cresyl phosphates. There have been numerous attempts to measure these substances, but the methodology generally requires sampling and submission to a laboratory, which does not permit real-time analysis. Furthermore, the existing methodologies typically require substantial dilutions of the samples that elevates the detection limit to µg/sample. Another group of toxic organo-phosphates are pesticides and nerve agents. Due to the extreme toxicity of these agents it would be desirable to detect the substances at the femtogram level, and develop equipment that can operate autonomously and record data in real-time.

BRIEF SUMMARY OF THE INVENTION

In view of the foregoing, an embodiment herein provides a system comprising a pump to deliver vapor comprising airborne contaminants comprising organic compounds comprising a target analyte; a collector to transfer the airborne contaminants by autonomous liquid extraction into a mobile organic liquid phase; a micro-fluidic chamber comprising immobilized biorecognition elements that bind to analytes delivered from the mobile organic liquid phase; a mechanism to introduce the mobile organic liquid phase to a buffer containing a plurality of substrates causing a series of biochemical reactions that create a change corresponding to a concentration of the target analyte; and a detector to perform real-time analysis that correlates to a concentration of the organic compounds to determine a presence of the target analyte.

The collector may comprise a tube comprising silica gel coated with a xerogel to collect the organic compounds. The collector may comprise a microelectromechanical systems (MEMS) device to collect the organic compounds. The system may comprise a reservoir to hold the mobile organic liquid phase; and a valve to control delivery of the mobile organic liquid phase into the collector, wherein the mobile organic liquid phase comprises a non-polar solvent. The non-polar solvent may comprise hexane. The system may comprise an alarm that is triggered upon detection of the presence of the target analyte above a predetermined level.

Another embodiment provides an apparatus comprising a collector to collect a plurality of organic classes of compounds from an air sample; a micro-fluidic chamber to combine the collected plurality of organic classes of compounds with a biochemically and chemically reactive mobile phase analytic solution; and a detector to detect a presence of phosphate compounds in the mobile phase analytic solution. The apparatus may comprise a column containing a xerogel coated silica gel to collect the plurality of organic classes of compounds; and a heater to heat the column.

The apparatus may comprise a MEMS device to collect the plurality of organic classes of compounds. The apparatus may comprise a microchannel reactor comprising immobilized acetylcholine esterase that is introduced to the collected plurality of organic classes of compounds and the mobile phase analytic solution. The detector may comprise a buffer to detect acetylcholine esterase activity and trigger a fluorescent-producing reaction and create a fluorophore upon detecting a presence of acetylcholine esterase that is inhibited by the phosphate compounds in the mobile phase analytic solution. The apparatus may comprise a light source to excite the fluorophore. The apparatus may comprise a photodiode to measure the fluorophore. The microchannel reactor may comprise a liquid chamber containing a drop-wise addition channel.

Another embodiment provides a method comprising converting acetylcholine to acetate and choline; oxidizing the choline to derive betaine aldehyde and hydrogen peroxide; oxidizing the hydrogen peroxide to generate a hydrogen ion and electron; and generating a fluorophore from the hydrogen ion and electron. The method may comprise introducing an enzyme comprising any of acetylcholine esterase, cyclooxygenase, and horseradish peroxidase to the acetylcholine to convert the acetylcholine to acetate and choline. The method may comprise immobilizing the enzyme. The method may comprise oxidizing the hydrogen peroxide by a peroxidase. The method may comprise exciting the fluorophore to fluorescence. The method may comprise correlating the fluorescence to an inverse correlation of a concentration of organo-phosphates.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 3 is a block diagram illustrating the gas-to-liquid transfer system of FIG. 1 with a reservoir and valve, according to an embodiment herein;

FIG. 5 is a block diagram illustrating an apparatus to perform gas-to-liquid transfer, according to an embodiment herein;

FIG. 6B is a block diagram illustrating the apparatus of FIG. 5 with a MEMS device, according to an embodiment herein;

FIG. 7 is a block diagram illustrating the apparatus of FIG. 5 with a microchannel reactor, according to an embodiment herein;

DETAILED DESCRIPTION OF THE INVENTION

Figure 1:
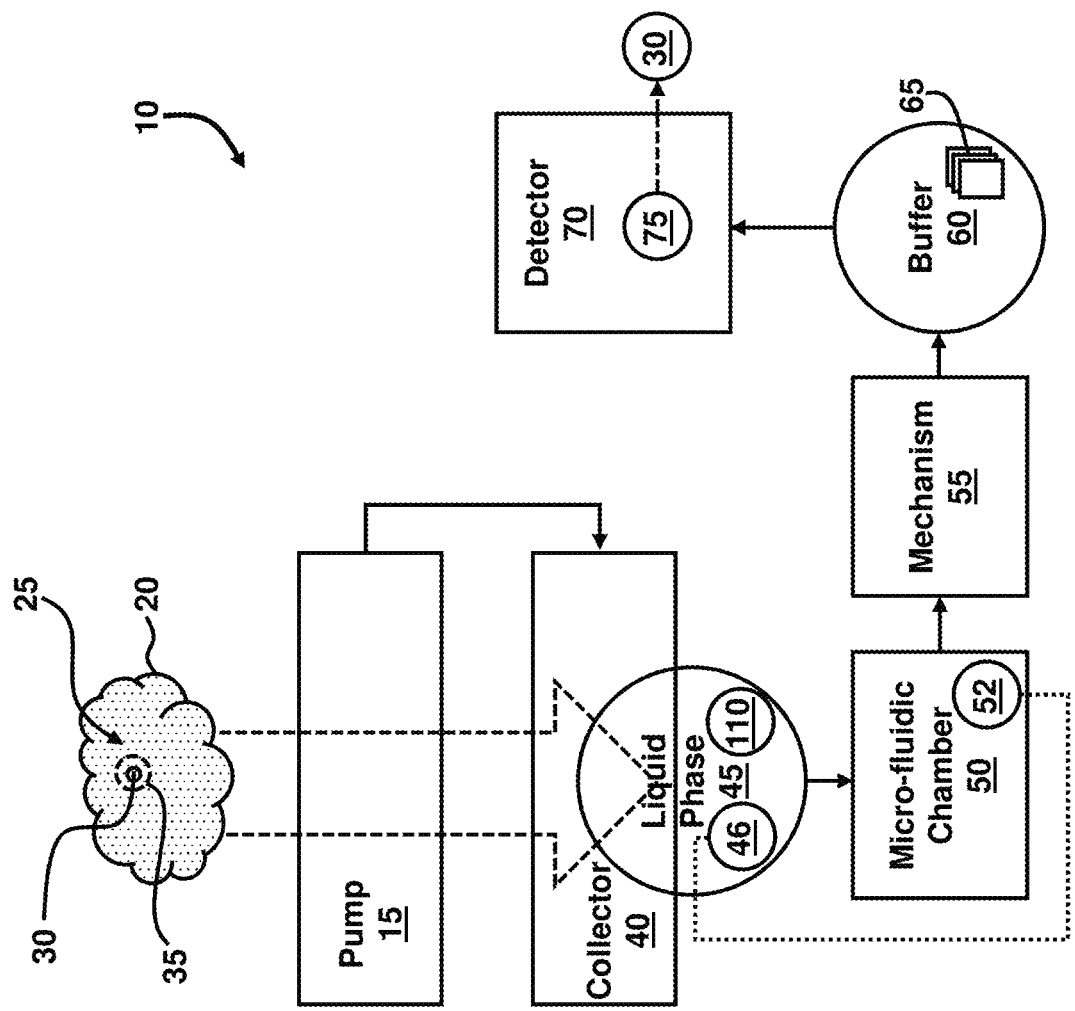
FIG. 1 is a block diagram illustrating a gas-to-liquid transfer system, according to an embodiment herein.

Embodiments of the disclosed invention, its various features and the advantageous details thereof, are explained more fully with reference to the non-limiting embodiments that are illustrated in the accompanying drawings and detailed in the following description. Descriptions of well-known components and processing techniques are omitted to not unnecessarily obscure what is being disclosed. Examples may be provided and when so provided are intended merely to facilitate an understanding of the ways in which the invention may be practiced and to further enable those of skill in the art to practice its various embodiments. Accordingly, examples should not be construed as limiting the scope of what is disclosed and otherwise claimed.

The embodiments herein provide a gas-to-liquid transfer system to detect the presence of contaminants such as organo-phosphate compounds, among others. A collector collects the air contaminants for transfer to a dual reaction liquid chamber liquid that adds a solvent, such as hexane, to the collected organo-phosphates. A detector is provided to detect the presence of phosphate compounds, for example, by introducing an enzyme such as acetylcholine esterase, cyclooxygenase, or horseradish peroxidase. The embodiments herein utilize fluorescence emissions or other detectors (i.e., electrochemical) to determine the presence of the contaminants.

Referring now to the drawings, and more particularly to FIGS. 1 through 23, where similar reference characters denote corresponding features consistently throughout, there are shown exemplary embodiments. In the drawings, the size and relative sizes of components, layers, and regions may be exaggerated for clarity.

FIG. 1 illustrates a system 10 comprising a pump 15 to deliver vapor 20 comprising airborne contaminants 25 comprising organic compounds 35 comprising a target analyte 30. The system 10 may be a portable system that is sized to be placed and removed from aircraft or other environmental location where air detection is required. In some examples, the pump 15 may comprise any of an electrical pump, mechanical pump, pneumatic pump, and electro-mechanical pump, or combinations thereof. The airborne contaminants 25 may comprise a plurality of different types of contaminants. In an example, the organic compounds 35 may comprise any of organo-phosphate compounds, opioids, cannabinoids, and other classes of organic compounds. The target analyte 30 may be selected based on a predetermined classification of target analytes that are desired to be detected and analyzed. Accordingly, the target analyte 30 comprises a chemical signature that the system 10 is configured to detect and analyze based on predetermined and/or pre-programmed chemical signature properties that are to be compared against to determine if there is a match, and the level of contamination or concentration of the target analyte 30 in the vapor 20.

The system 10 further comprises a collector 40 to transfer the airborne contaminants 25 by autonomous liquid extraction into a mobile organic liquid phase 45. In an example, the collector 40 may comprise a gas-to-liquid collector that utilizes collection gels, beads, or other mechanisms to collect the airborne contaminants 25 for transfer by liquid extraction. The mobile organic liquid phase 45 may flow at any suitable rate necessary to carry the liquid phase of the airborne contaminants 25 and corresponding organic compounds 35. In an example, the mobile organic liquid phase 45 may comprise a non-polar solvent 110. For example, the non-polar solvent 110 may comprise hexane or any other suitable non-polar material.

The system 10 comprises a micro-fluidic chamber 50 comprising immobilized biorecognition elements 52 that bind to analytes 46 delivered from the mobile organic liquid phase 45. For example, the biorecognition elements 52 may be natural or synthetic. In some examples, the biorecognition elements 52 may include antibody enzymes, nucleic acid aptamers, or molecularly imprinted polymers. Unbound biorecognition elements 52 (i.e., free of the target analyte 30) compared to biorecognition elements 52 bound with target analytes 30 detection. According to the embodiments herein, reagents (not shown) are added in an aqueous phase (e.g., oil in water droplet) to trigger reactions needed for detection of the target analyte 30. For example, the reagents may include Amplex® red reagent, among others. The micro-fluidic chamber 50 may contain a micro-preconcentrator (µ-PC) device (not shown in FIG. 1) to control the concentration levels of the organic compounds 35 to be utilized for testing and analysis in the system 10. For example, the micro-fluidic chamber 50 and the µ-PC device may be used to increase the concentration of the organic compounds 35 (and thus, the target analytes 30) from a lower concentration to a higher concentration.

The system 10 may comprise a mechanism 55 to introduce the mobile organic liquid phase 45 to a buffer 60 containing a plurality of substrates 65 causing a series of biochemical reactions that create a change corresponding to a concentration of the target analyte 30. In an example, the mobile organic liquid phase 45 may be introduced by drop-wise addition, and thus the mechanism 55 may be any suitable device, such as a mechanical dropper, that transfers the mobile organic liquid phase 45 to the buffer 60. The buffer 60 may be any suitable type of buffering solution to control some of the chemical properties associated with the mobile organic liquid phase 45, such as the acidity, etc. For example, the buffer 60 may comprise any of acetylcholine esterase, cyclooxygenase, and horseradish peroxidase reacting with the acetylcholine to convert the acetylcholine to acetate and choline. The plurality of substrates 65 may comprise any suitable type of chemical material or molecules upon which the enzymes in the mobile organic liquid phase 45 act including bonding. The system 10 further comprises a detector 70 to perform real-time analysis 75 that correlates to a concentration of the organic compounds 35 to determine a presence of the target analyte 30. In an example, the detector 70 may comprise a photodetector configured to detect of fluorescence emission. Moreover, the detector 70 may comprise any of an electronic, electrochemical, plasmonic, surface plasmon resonance, absorption, emission, electron transfer, and charge transfer device, or combinations thereof, or any other suitable detection system. The detector 70 may comprise a processor or may be communicatively linked to a processor, computer, or server device(s) to perform the real-time analysis 75 of the organic compounds 35 in order to determine the presence of the target analyte 30.

In an alternative embodiment, instead of enzymes generating a read-out, the analytes of interest (e.g., target analyte 30) can interact with the biorecognition elements 52, freeing them from the surface of a microreactor. These biorecognition elements 52 can then be detected downstream using the detector 70 with or without capture.

Figure 2A:
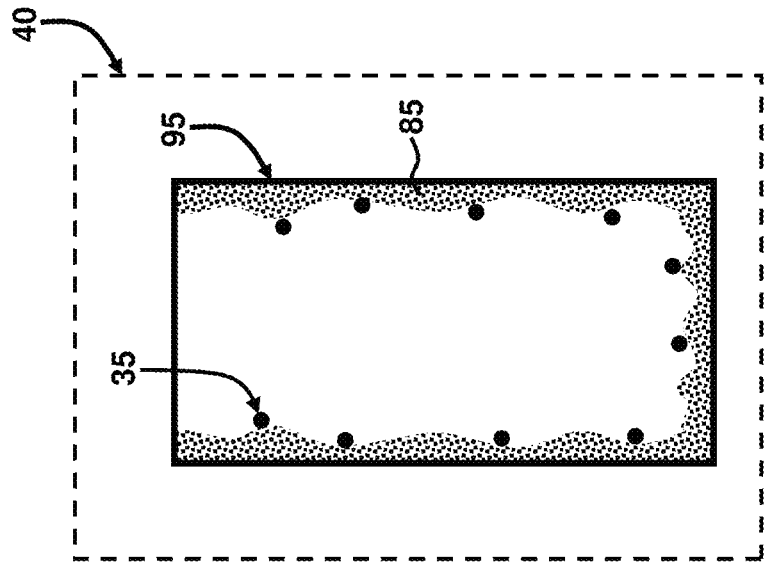
FIG. 2A is a block diagram illustrating the collector of the gas-to-liquid transfer system of FIG. 1 with a tube, according to an embodiment herein.

FIG. 2A, with reference to FIG. 1, illustrates that the collector 40 may comprise a tube 80 comprising silica gel 85 coated with a xerogel 90 to collect the organic compounds 35. The tube 80 may comprise any suitable size or material such as glass or durable plastic, for example. In an example, the silica gel 85 coated with the xerogel 90 may comprise solid pellets that are positioned in the tube 80. In another example, the silica gel 85 may comprise viscous gel or material with the xerogel 90 coated thereon, and which are positioned in the tube 80. Accordingly, the embodiments herein are not restricted to any particular configuration of the silica gel 85 and/or xerogel 90. The FIG. 2B, with reference to FIGS. 1 and 2A, illustrates that the collector 40 may comprise a MEMS device 95 to collect the organic compounds 35. A non-limiting example of a MEMS device/system that could be used for the MEMS device 95 herein is described in Bae, B., et al., "A Fully-Integrated MEMS Preconcentrator for Rapid Gas Sampling," U.S. Air Force Report AFRL-PR-WP-TP-2007-224 for submission of a Conference paper submitted to the Proceedings of the Transducers 2007 Conference, Mar. 19, 2007, pp. 1-4, the complete disclosure of which, in its entirety, is herein incorporated by reference.

Figure 2B:
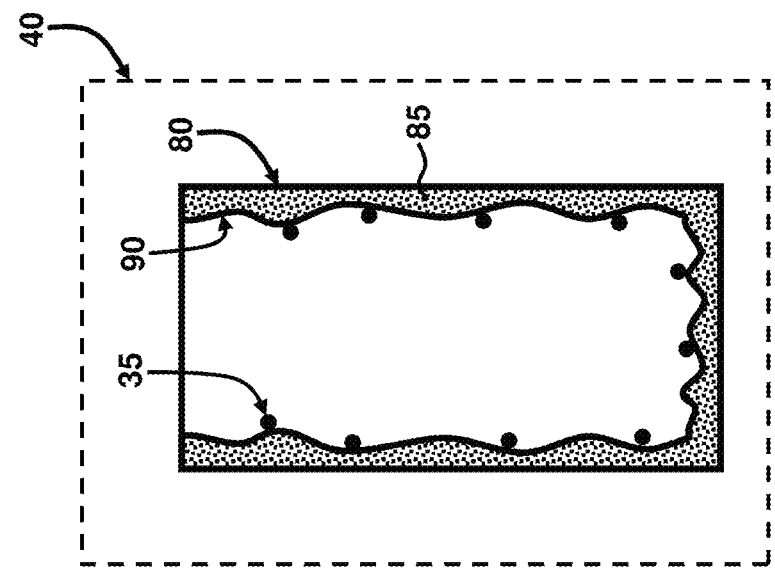
FIG. 2B is a block diagram illustrating the collector of the gas-to-liquid transfer system of FIG. 1 with a MEMS device, according to an embodiment herein.

FIG. 3, with reference to FIGS. 1 through 2B, illustrates that the system 10 may comprise a reservoir 100 to hold the mobile organic liquid phase 45. The reservoir 100 may be any suitable type of liquid chromatographic instrument that may be configured to retain the mobile organic liquid phase 45. In an example, the reservoir may be configured to contain pressurized solvent and may comprise vacuum connections for drawing the mobile organic liquid phase 45 therefrom and/or thereto.

Figure 4:
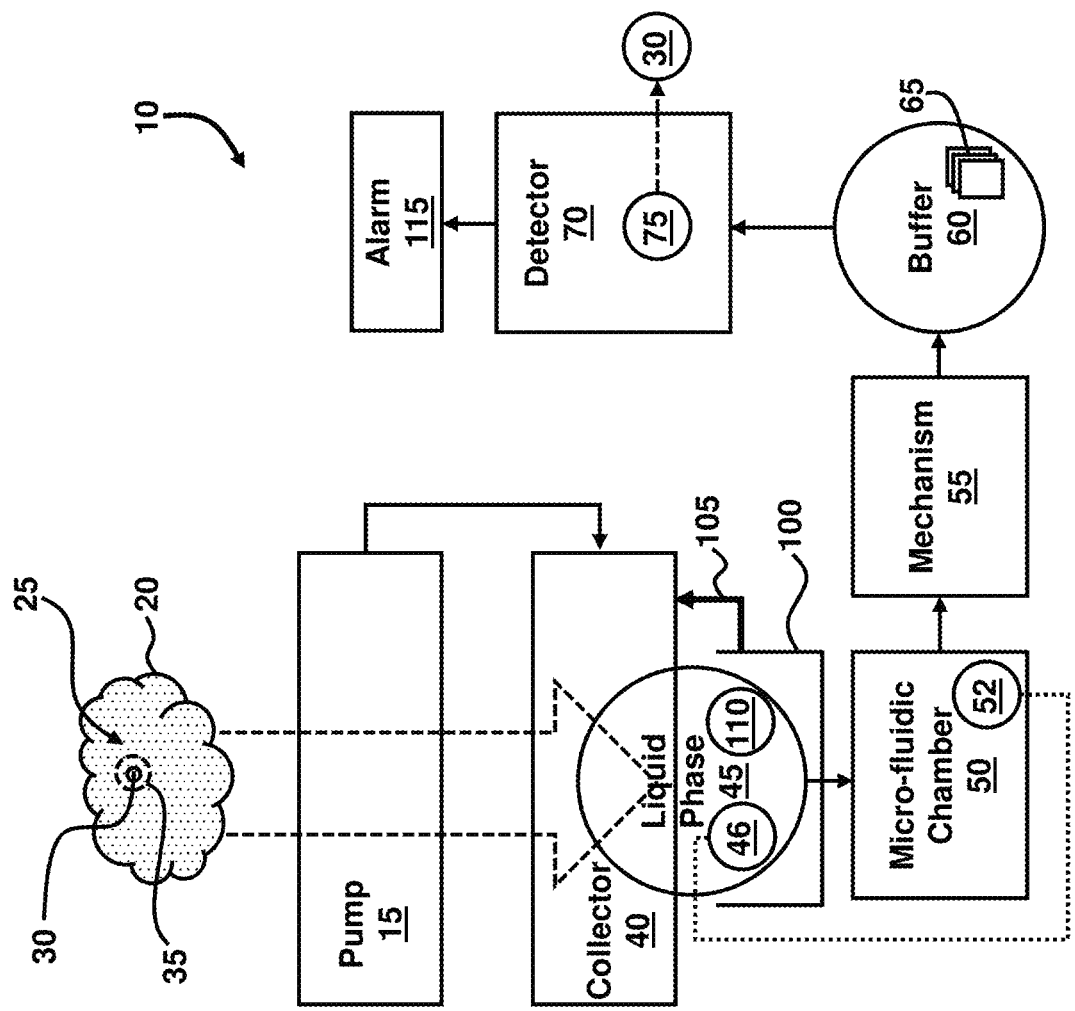
FIG. 4 is a block diagram illustrating the gas-to-liquid transfer system of FIG. 1 with an alarm, according to an embodiment herein.

The system 10 may comprise a valve 105 to control delivery of the mobile organic liquid phase 45 into the collector 40. The valve 105 may comprise any suitable type of electrical, mechanical, pneumatic, or electro-mechanical valve, or combinations thereof. Moreover, the valve 105 may be automatically controlled by a local or remote processor or controller (not shown) or controlled by user intervention, as necessary. FIG. 4, with reference to FIGS. 1 through 3, illustrates that the system 10 may comprise an alarm 115 that is triggered upon detection of the presence of the target analyte 30 above a predetermined level. The alarm 115 may comprise any of an audio alarm, visual alarm, or combinations thereof. The alarm 115 may be communicatively coupled to the detector 70 and/or a processor or computer that transmits a signal to the alarm 115 upon the detector 70 detecting the presence of the target analyte 30 above a pre-programmed predetermined level. Since the detection and analysis of the presence of the target analyte 30 occurs in real-time, the alarm 115 is also triggered in real-time to alert users (i.e., pilots or other aircraft personnel, for example) to exit the aircraft or otherwise take precautionary measures to protect themselves from a potentially toxic environment due to the presence of the target analyte 30. Moreover, the alarm 115 may comprise variable outputs based on the level of the presence of the target analyte 30. For example, a yellow light may be output to indicate the presence of the target analyte 30 at levels that are not considered immediate health threats. Alternatively, a red light may be output to indicate a significant health threat to personnel in the vicinity of the system 10 and vapor 20. Similarly, the variable outputs may be audio-based with different pitches, tones, or frequencies depending on the level of the threat that is detected. In another example, the audio output from the alarm 115 may be a computer-generated voice providing instructions for personnel as well as outputting the type of target analyte 30 that has been detected as well as the level (i.e., amount) of detection.

FIG. 5, with reference to FIGS. 1 through 4, illustrates another embodiment that provides an apparatus 150 comprising a collector 40 to collect a plurality of organic classes of compounds 155 from an air sample 160. The apparatus 150 may be miniaturized to be portable and easily transferred from various settings such as aircraft, for example. The plurality of organic classes of compounds 155 may comprise any of organo-phosphate compounds, opioids, cannabinoids, and other classes of organic compounds, according to some examples. The air sample 160 may be the ambient air in an aircraft cockpit, for example. However, the air sample 160 and corresponding environmental location for using the apparatus 150 may be any suitable location where the detection and analysis of the air sample 160 is required.

The apparatus 150 comprises a micro-fluidic chamber 50 to combine the collected plurality of organic classes of compounds 155 with a biochemically and chemically reactive mobile phase analytic solution 170 (e.g., which may be the buffer 60 containing the plurality of substrates 65, for example). According to an example, single or multiple pairs of immiscible liquids may extract and transfer contaminants to the biochemically and chemically reactive mobile phase analytic solution 170. The apparatus 150 further comprises a detector 70 to detect a presence of phosphate compounds 175 in the mobile phase analytic solution 170. As such, the mobile phase analytic solution 170 may be any suitable type of buffering solution to control chemical properties, and may contain any suitable type of chemical material or molecules upon which enzymes act, including bonding. In an example, the mobile phase analytic solution 170 may comprise the mobile organic liquid phase 45, described above, of the collected plurality of organic classes of compounds 155.

Figure 6A:
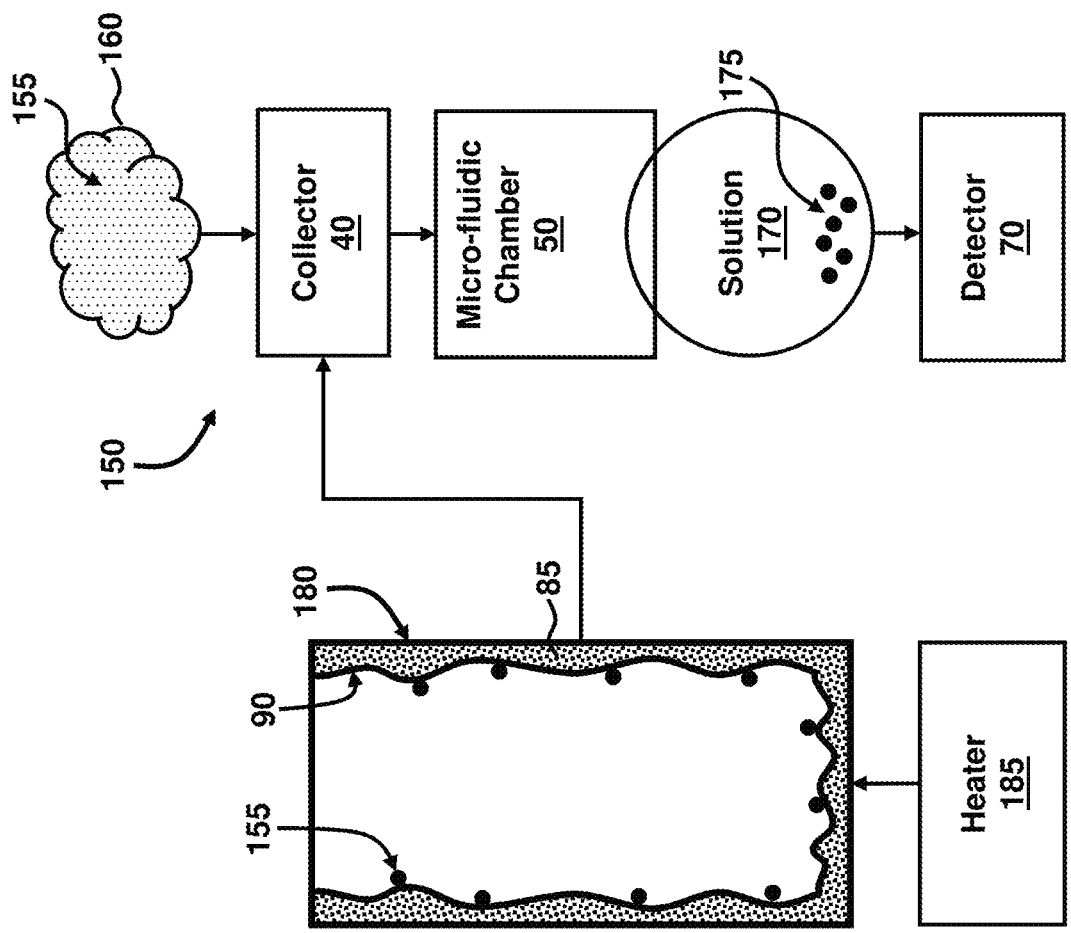
FIG. 6A is a block diagram illustrating the apparatus of FIG. 5 with a column and heater, according to an embodiment herein.

FIG. 6A, with reference to FIGS. 1 through 5, illustrates that the apparatus 150 may comprise a column 180 containing a xerogel 90 coated silica gel 85 to collect the plurality of organic classes of compounds 155. The column 180 may comprise any suitable size or material such as glass or durable plastic, for example. In an example, the silica gel 85 is coated with the xerogel 90 and may comprise solid pellets that are positioned in the column 180. In another example, the silica gel 85 may comprise viscous gel or material with the xerogel 90 coated thereon, and which are positioned in the column 180. According to an example, the column 180 may be configured to withstand pressured liquids including the mobile phase analytic solution 170, the mobile organic liquid phase 45, or other liquids, solvents, or solutions. The apparatus 150 may comprise a heater 185 to heat the column 180. The heater 185 may comprise any suitable type of heater 185 that can be automatically and/or manually controlled to heat the column 180 to desired temperatures. In an example, the heater 185 may be used to heat to the column 180 to help facilitate a separation process of the mobile phase analytic solution 170.

FIG. 6B, with reference to FIGS. 1 through 6A, illustrates that the apparatus 150 may comprise a MEMS device 95 to collect the plurality of organic classes of compounds 155. FIG. 7, with reference to FIGS. 1 through 6B, illustrates that the apparatus 150 may comprise a microchannel reactor 190 comprising immobilized acetylcholine esterase 195 or other alternative selective enzyme or aptamer that is inhibited by the phosphate compounds 175 that is introduced to the collected plurality of organic classes of compounds 155 and the mobile phase analytic solution 170. According to an example, the microchannel reactor 190 may comprise a continuous plug flow reactor, although other types of reactors may be utilized in accordance with the embodiments herein. The microchannel reactor 190 may comprise a series of serpentine channels in which the chemical reactions of the mobile phase analytic solution 170 occur. Moreover, the microchannel reactor 190 may be configured to have suitable heat exchange thermal properties to withstand exothermic reactions of the mobile phase analytic solution 170.

Figure 8:
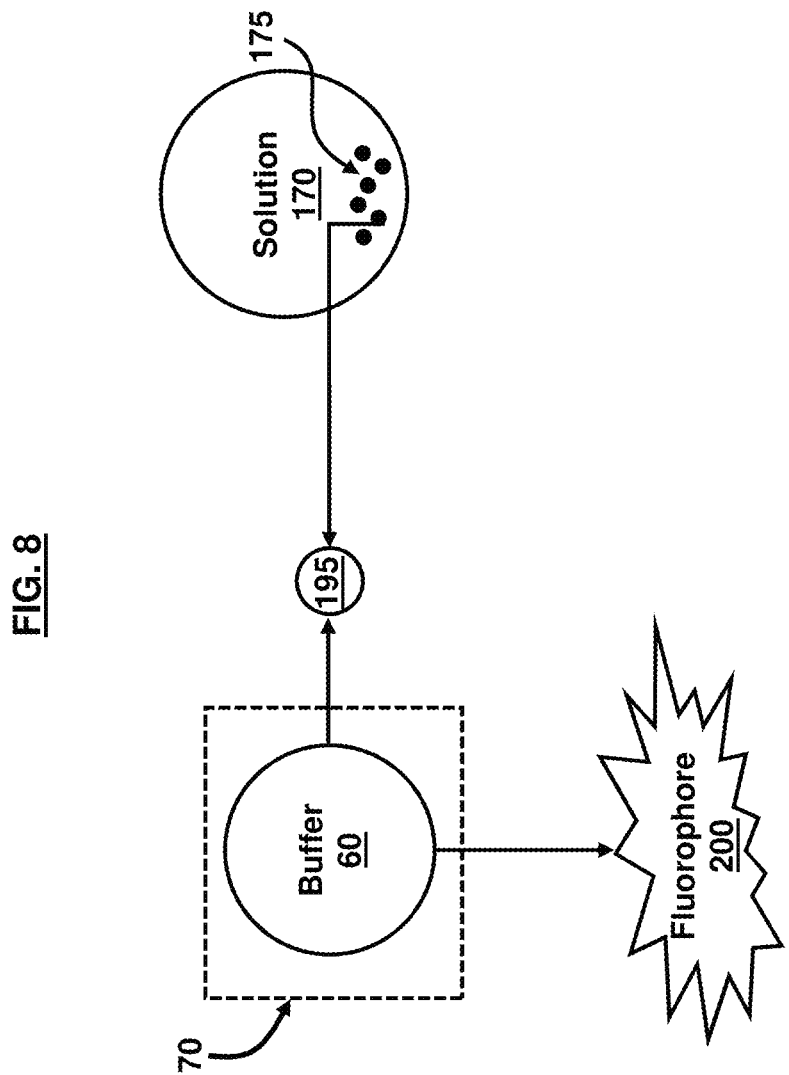
FIG. 8 is a block diagram illustrating aspects of the detector of the apparatus of FIG. 5, according to an embodiment herein.

FIG. 8, with reference to FIGS. 1 through 7, illustrates that the detector 70 may comprise a buffer 60. As described above, and in some examples, the buffer 60 may comprise any of acetylcholine esterase, cyclooxygenase, and horseradish peroxidase reacting with the acetylcholine to convert the acetylcholine to acetate and choline. The buffer 60 is to detect acetylcholine esterase activity and trigger a fluorescent-producing reaction and create a fluorophore 200 upon detecting a presence of acetylcholine esterase 195 that is inhibited by the phosphate compounds 175 in the mobile phase analytic solution 170 resulting in a quenching of the enzyme comprising any of the acetylcholine esterase, cyclooxygenase, and horseradish peroxidase. The fluorophore 200 may be any suitable type of fluorescent chemical compound capable of re-emitting light upon excitation caused by the reaction of the buffer 60.

Figure 9:
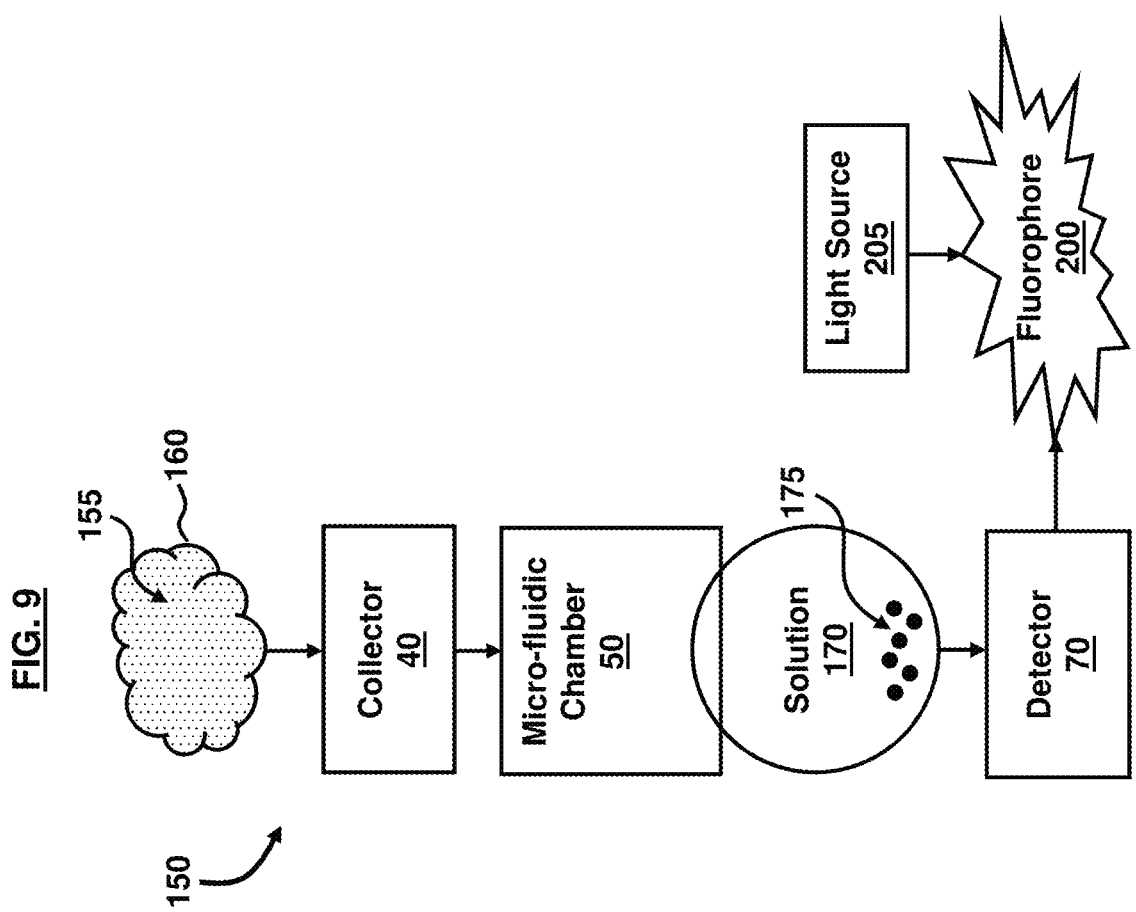
FIG. 9 is a block diagram illustrating the apparatus of FIG. 5 with a light source, according to an embodiment herein.
Figure 10:
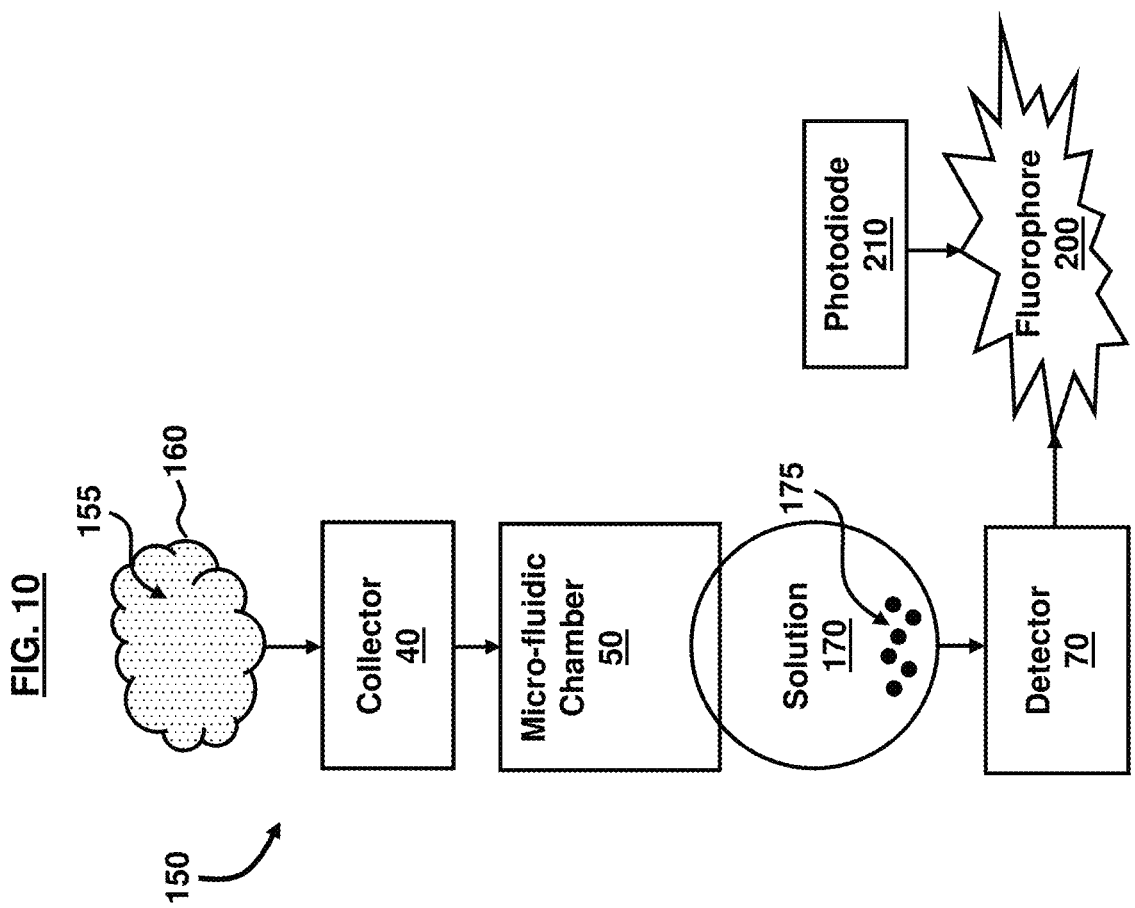
FIG. 10 is a block diagram illustrating the apparatus of FIG. 5 with a photodiode, according to an embodiment herein.
Figure 11:
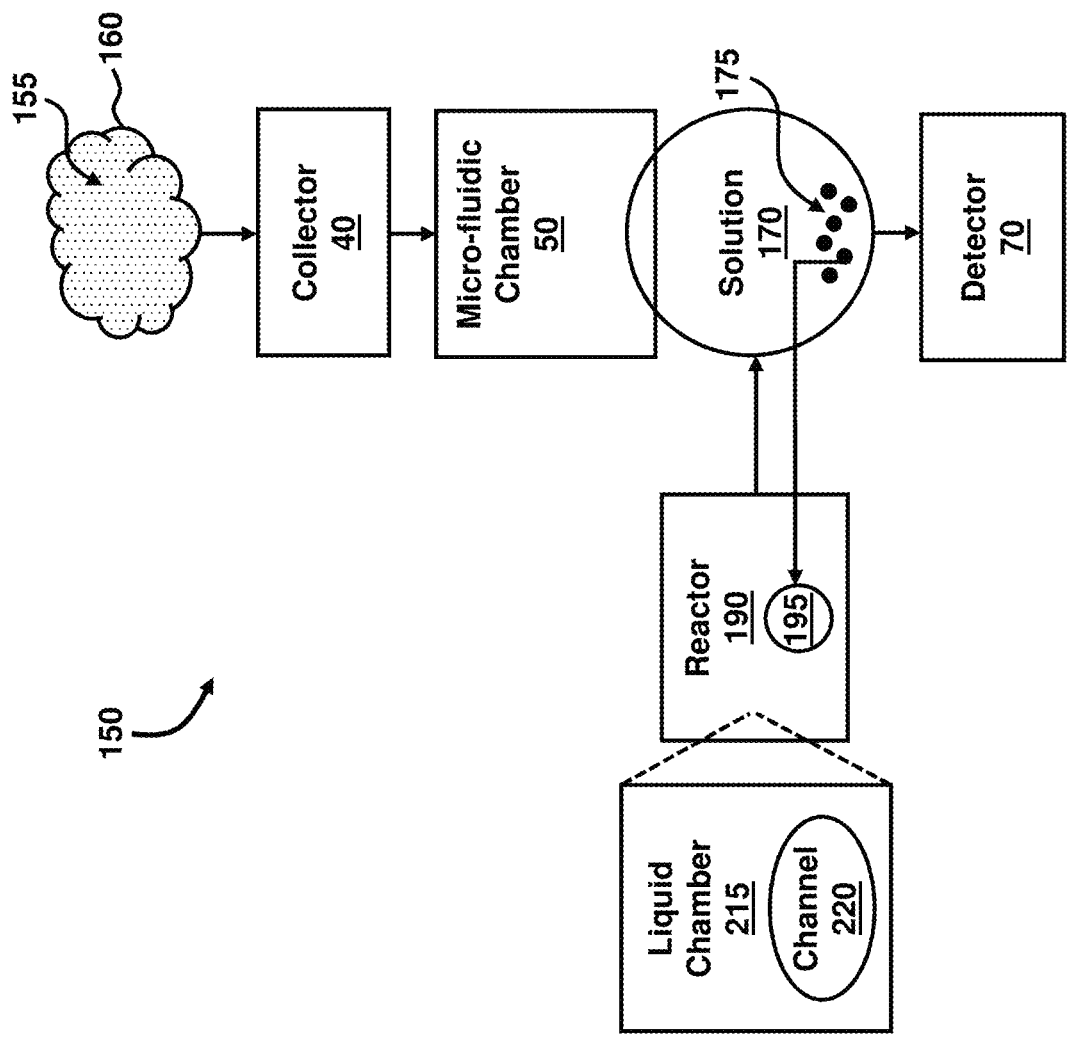
FIG. 11 is a block diagram illustrating aspects of the microchannel reactor of the apparatus of FIG. 5, according to an embodiment herein.

FIG. 9, with reference to FIGS. 1 through 8, illustrates that apparatus 150 may comprise a light source 205 to excite the fluorophore 200. In an example, the light source 205 may comprise a light-emitting diode (LED) or any other suitable light generating and emitting device. FIG. 10, with reference to FIGS. 1 through 9, illustrates that apparatus 150 may comprise a photodiode 210 to measure the fluorophore 200. The photodiode 210 may be configured to measure the light emitted by the fluorophore 200 and convert the light into an electrical current. According to an example, the concentration of the phosphate compounds 175 is inversely proportional to the excitation of the fluorophore 200, which indicates the presence of the toxins (based on a predetermined chemical signature as described above) from the plurality of organic classes of compounds 155 in the air sample 160. FIG. 11, with reference to FIGS. 1 through 10, illustrates that microchannel reactor 190 may comprise a liquid chamber 215 containing a drop-wise addition channel 220, according to an example. The liquid chamber 215 and drop-wise addition channel 220 may be any suitable devices and instruments capable of retaining and transferring the aforementioned solvents and solutions used in the apparatus 150.

Figure 12A:
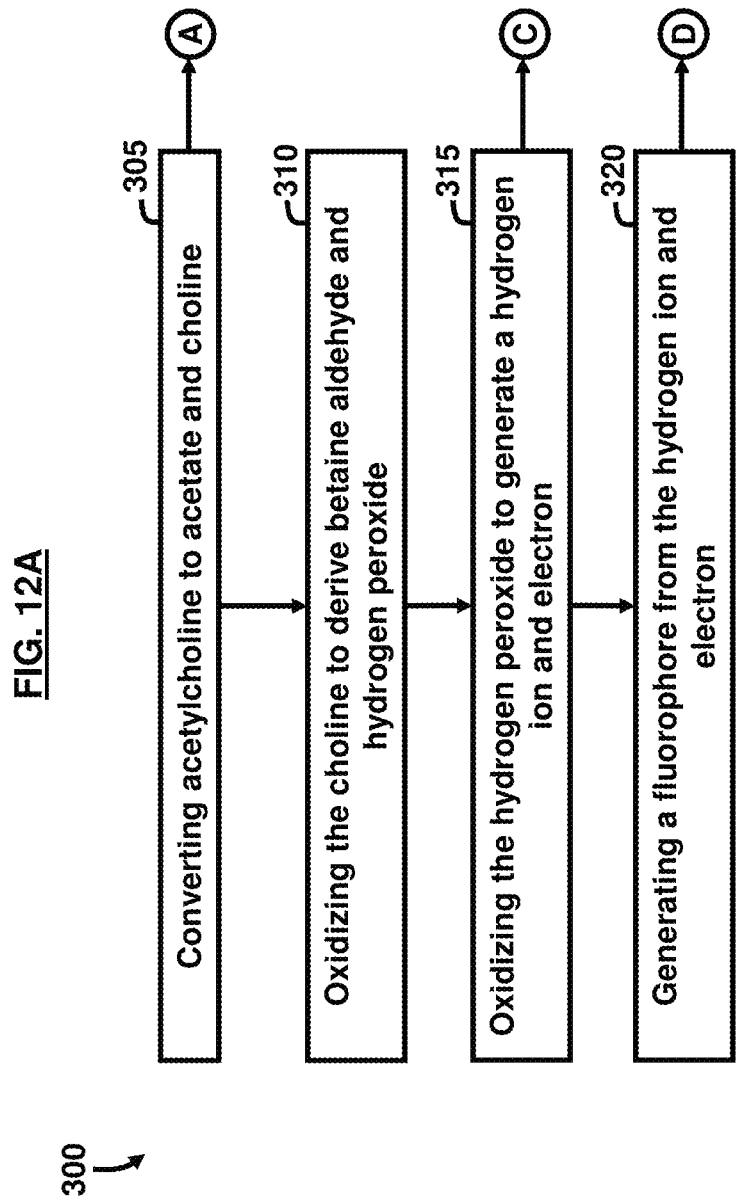
FIG. 12A is a flow diagram illustrating a method of performing a chemical process, according to an embodiment herein.
Figure 12B:
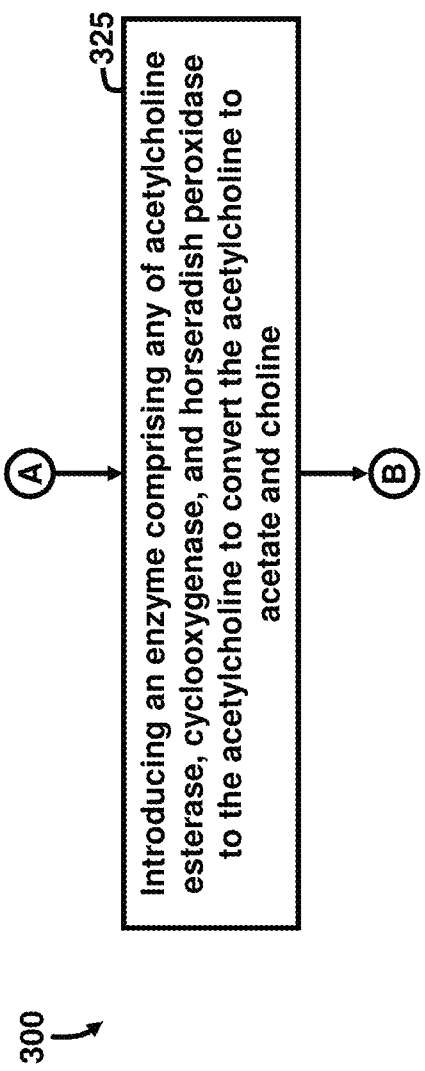
FIG. 12B is a flow diagram illustrating a method of introducing an enzyme in the chemical process of FIG. 12A, according to an embodiment herein.
Figure 12C:
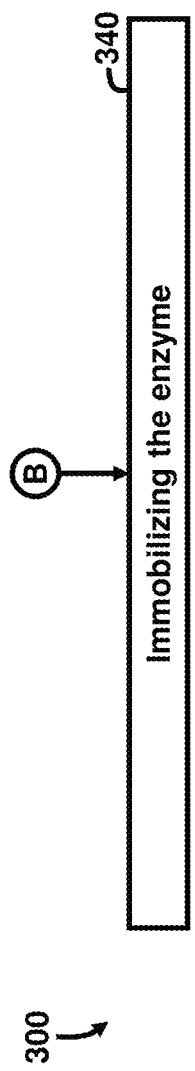
FIG. 12C is a flow diagram illustrating a method of immobilizing an enzyme in the chemical process of FIG. 12B, according to an embodiment herein.
Figure 12D:
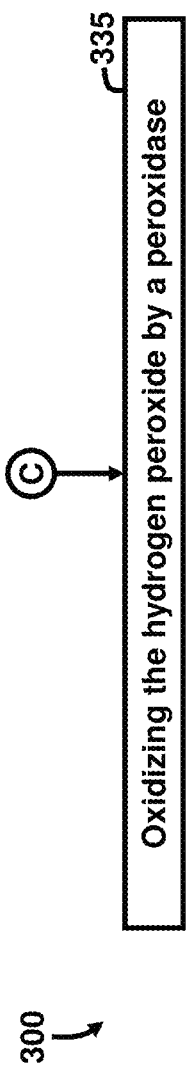
FIG. 12D is a flow diagram illustrating a method of oxidizing the hydrogen peroxide in the chemical process of FIG. 12A, according to an embodiment herein.
Figure 12E:
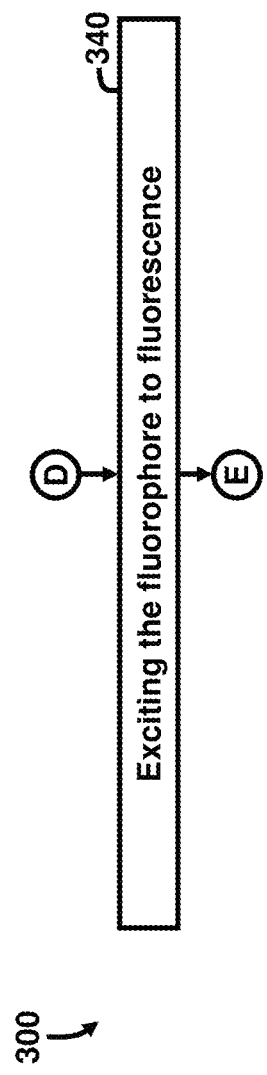
FIG. 12E is a flow diagram illustrating a method of exciting the fluorophore in the chemical process of FIG. 12A, according to an embodiment herein.
Figure 12F:
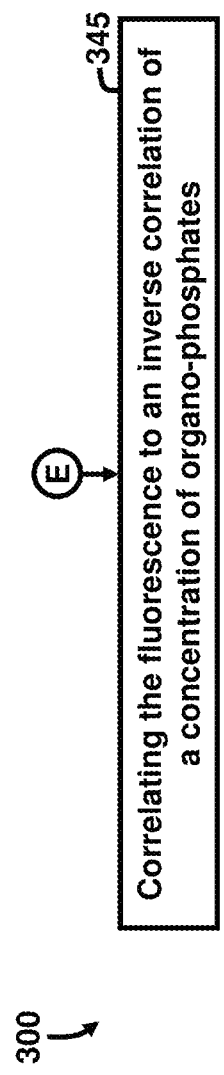
FIG. 12F is a flow diagram illustrating a method of correlating a fluorescence in the chemical process of FIG. 12A, according to an embodiment herein.
Figure 13:
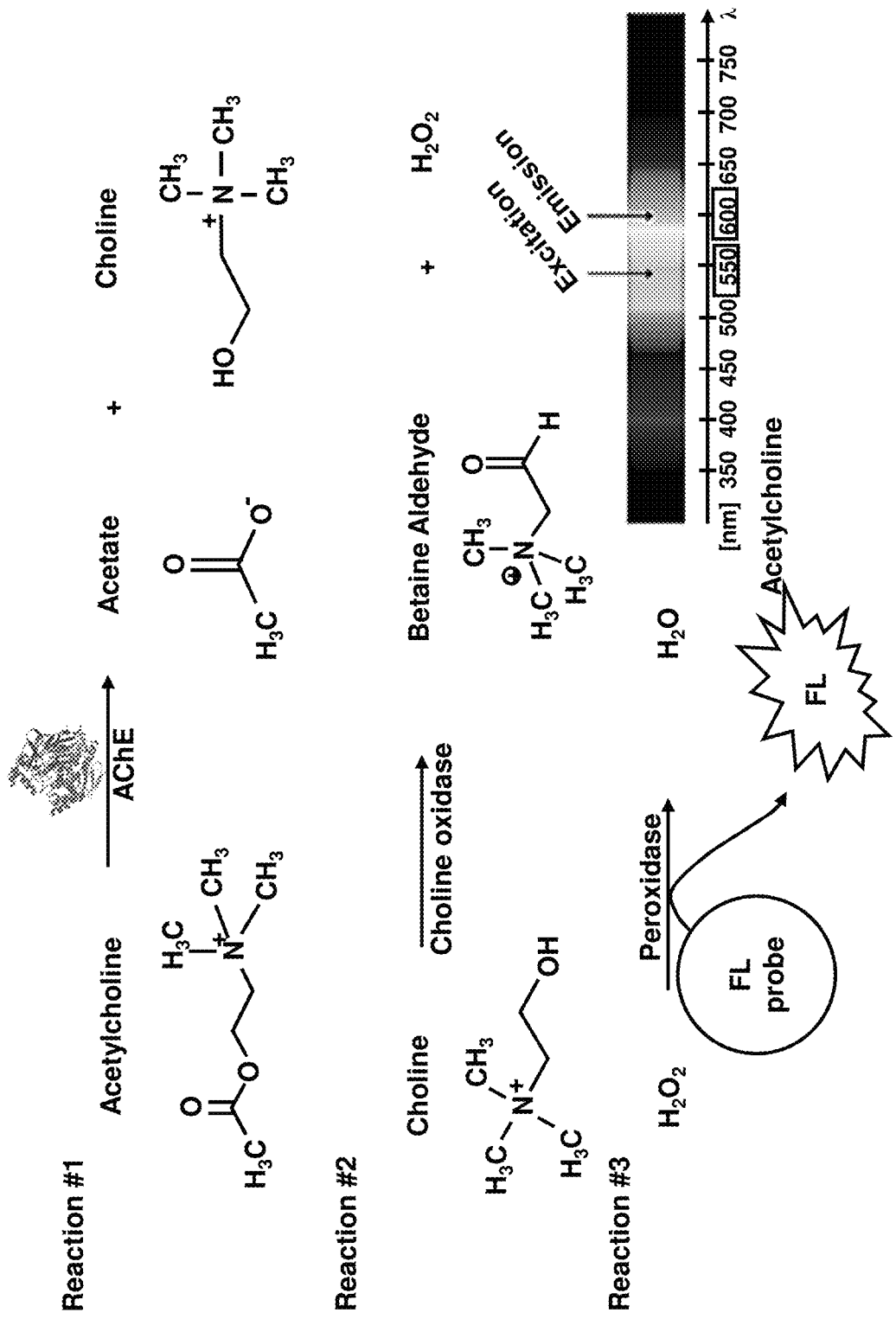
FIG. 13 is a schematic representation of the chemical process of the method of FIG. 12A, according to an embodiment herein.

FIG. 12A, with reference to FIGS. 1 through 11, is a flow diagram illustrating a method 300 according to an embodiment herein. FIG. 13 illustrates a schematic representation of the chemical process described by the method 300. According to an example, the method 300 comprises converting (305) acetylcholine to acetate and choline; oxidizing (310) the choline to derive betaine aldehyde and hydrogen peroxide; oxidizing (315) the hydrogen peroxide to generate a hydrogen ion and electron; and generating (320) a fluorophore 200 from the hydrogen ion and electron. FIG. 12B, with reference to FIGS. 1 through 12A, is a flow diagram illustrating that the method 300 may comprise introducing (325) an enzyme comprising any of acetylcholine esterase, cyclooxygenase, and horseradish peroxidase to the acetylcholine to convert the acetylcholine to acetate and choline. FIG. 12C, with reference to FIGS. 1 through 12B, is a flow diagram illustrating that the method 300 may comprise immobilizing (330) the enzyme. FIG. 12D, with reference to FIGS. 1 through 12C, is a flow diagram illustrating that the method 300 may comprise oxidizing (335) the hydrogen peroxide by a peroxidase. FIG. 12E, with reference to FIGS. 1 through 12D, is a flow diagram illustrating that the method 300 may comprise exciting (340) the fluorophore 200 to fluorescence. FIG. 12F, with reference to FIGS. 1 through 12E, is a flow diagram illustrating that the method 300 may comprise correlating (345) the fluorescence to an inverse correlation of a concentration of organo-phosphates.

AChE is an important enzyme that breaks down acetylcholine, a key substance as a neurotransmitter. Organophosphates are toxic because they inhibit AChE activity by binding on the active site of AChE covalently. The embodiments herein provide an inhibition mechanism to detect the organo-phosphate in the air, as depicted in FIG. 13, with reference to FIGS. 1 through 12F. There are three reactions which are concerned with three enzymes of AChE, COX, and HRP. Reaction 1 is a degradation reaction that converts acetylcholine to acetate and choline with AChE. Reaction 2 is an oxidation reaction of choline in which betaine aldehyde and hydrogen peroxide are derived, and the hydrogen peroxide is oxidized by peroxidase to generate hydrogen ion and electron. The hydrogen and electron activate the fluorescence substrate. The fluorescence is excited at 550 nm and 600 nm light is emitted.

The embodiments herein were experimentally tested according to the following series of experiments. The specific devices, orientations, configurations, geometries, sizes, temperatures, timings, ratios, speeds, techniques, colors, and/or types and amounts of materials, etc. described in the experiments below are merely exemplary, and the embodiments herein are not restricted to any particular structure, property, technique, or material described below. Accordingly, the experiments are merely being presented to demonstrate the feasibility of the embodiments herein and are not meant to restrict how the invention may be practiced.

Experiments

Figure 14B:
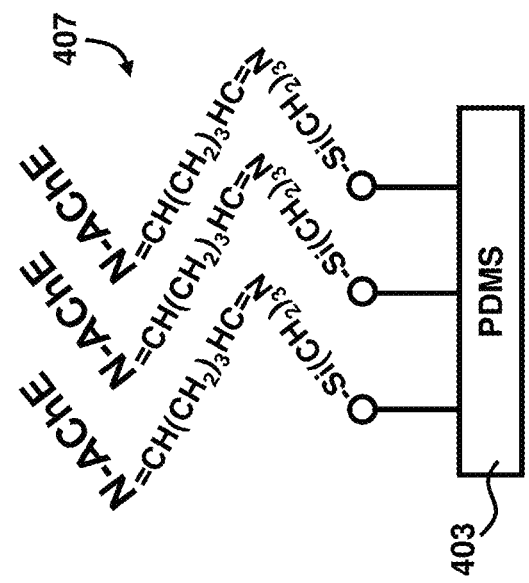
FIG. 14B is a schematic diagram illustrating a chemical scheme of the enzyme immobilization structure, according to an embodiment herein.
Figure 14A:
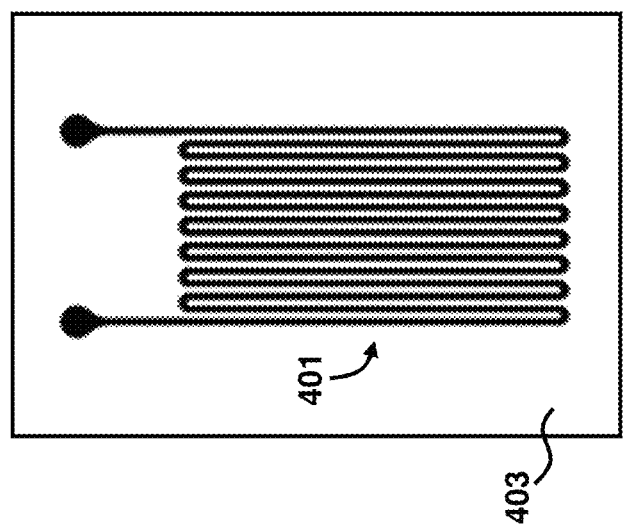
FIG. 14A is a schematic diagram illustrating a microfluidic device, according to an embodiment herein.

The microchannel reactor 190 may comprise a serpentine microfluidic channel 401 as depicted in FIG. 14A, and which may be fabricated by soft-lithography processing. For example, photo-lithography is used to make the mold, and white polydimethylsiloxane (PDMS, 1:10 ratio of cross linker and monomer) 403 is cured on the mold at 70° C. after spin coating at 250 RPM. The microfluidic channel 401 formed by soft-lithography is then covered with a transparent slab of PDMS 403. The surface of the microfluidic channel 401 is exposed to UV-plasma to generate hydroxyl groups on the surface, to allow functionalization with amine groups via (3-aminopropyl) triethoxylane (3-APTES). Acetone and 3-APTES are mixed at a 7:3 ratios, and injected into the microfluidic channel 401 at a 100 µL/min flow rate at approximately 60° C. for approximately 4 hours. After functionalization, a cross-linker is developed using glutaraldehyde at a 6:4 ratio of PBS (phosphate buffer saline) and glutaraldehyde mixture (glutaraldehyde 10% in PBS) and injected at ~50 µL/min flow rate for approximately 4 hours. Finally, enzymes of acetylcholinesterase (AChE, ~12.5 choline oxidase (COX, ~12.5 µL/mL), and horseradish peroxidase (HRP, ~5 µL/mL) are immobilized on the surface of the microfluidic channel 401. FIG. 14B shows the chemical scheme of the enzyme immobilization structure 407 on the PDMS 403. The prepared microchannel reactor 190 is filled with PBS and stored at approximately 4° C. The chain reaction using the microchannel reactor 190 is performed with reactant mixtures of acetylcholine (~100 µM) and fluorescence substance (~5 µL) as the mixture is injected into the microchannel reactor 190 at ~200 µL/min flow rate at approximately 30° C. Fluorescence from the reaction is excited at ~550 nm wavelength (~green light), and emitted at ~600 nm (~orange light).

Figure 14D:
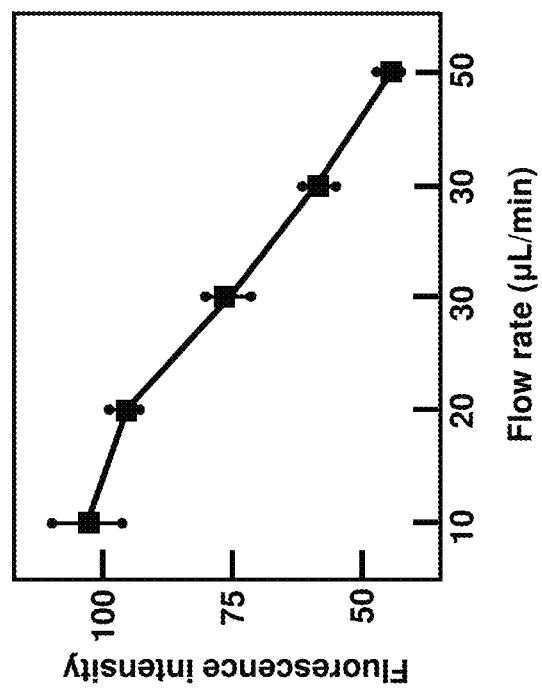
FIG. 14D is a graphical representation that correlates the fluorescence intensity as a function of flow rate, according to an embodiment herein.
Figure 14C:
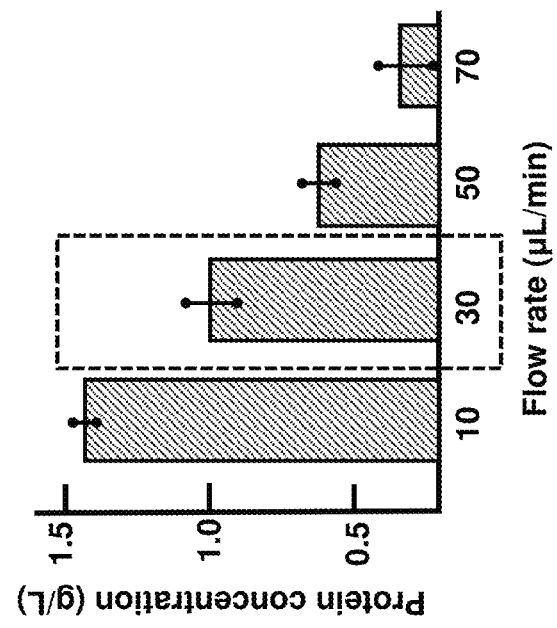
FIG. 14C is a graphical representation that correlates the protein concentration as a function of flow rate, according to an embodiment herein.

The microchannel reactor 190 is prepared as all enzymes are immobilized on the surface of the channel 401. The cross-linker quantity and enzyme binding amount are controlled by changing functionalization time and flow rate. FIG. 14C depicts the flow rate results. High enzyme immobilization level leads to high enzyme activity in the microchannel reactor 190. Excessively high activity, however, leads to saturation in the fluorescence intensity, and such high activity can dilute the effect of organo-phosphate inhibition. Such competitive inhibition is usually solved with excessive enzyme amount. Thus, an appropriate enzyme amount should be immobilized to for high sensitivity of organo-phosphate inhibition. As with the functionalization time, the quantity of cross-linker can be varied. For high sensitivity of inhibition response, the functionalization time is determined at over 2 hours. The flow rate for enzyme immobilization is ~30 µL/min as denoted by the dashed box in FIG. 14C. If a high level of protein is immobilized, the sensitivity decreases. A flow rate of 30 µL/min yields an appropriate reaction rate. Fluorescence is very sensitive, and it shows reasonable intensity with µmon concentration level of acetylcholine. When the flow rate is ~30 µL/min, the relative fluorescence intensity is ~75% of saturated intensity as indicated in the results of FIG. 14D.

The collector 40 may be an air-to-liquid (gas-to-liquid) tributyl phosphate (TBP) collector 40. The TBP collection may include a gas-to-liquid extractor that is utilized in a laboratory hood. A beaker containing ~10 mL TBP is placed adjacent to a probe on the TBP collector 40. The collector 40 sniffs TBP, and the membrane is rinsed with hexane. The TBP on the membrane dissolves in hexane, and finally the TBP can be collected in a 1 mL syringe for injection into the reaction-detection system.

Figure 15A:
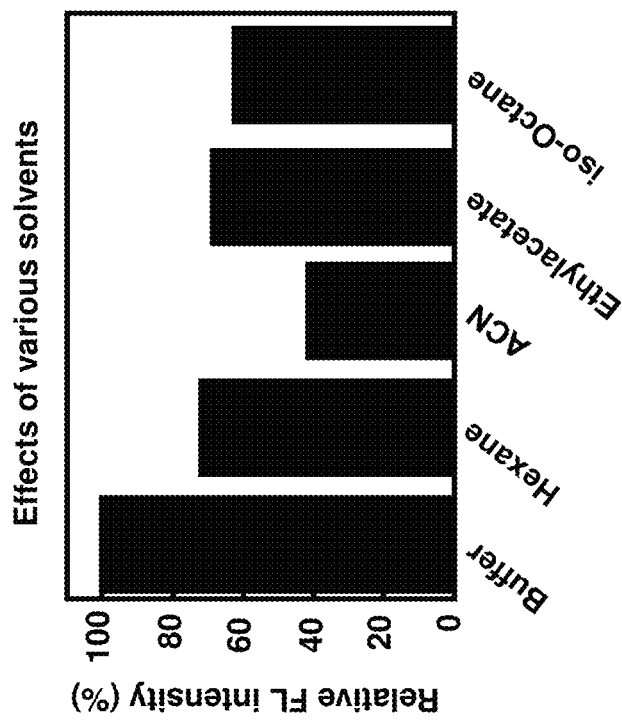
FIG. 15A is a graphical representation that illustrates the relative fluorophore intensity for various solvents, according to an embodiment herein.
Figure 15B:
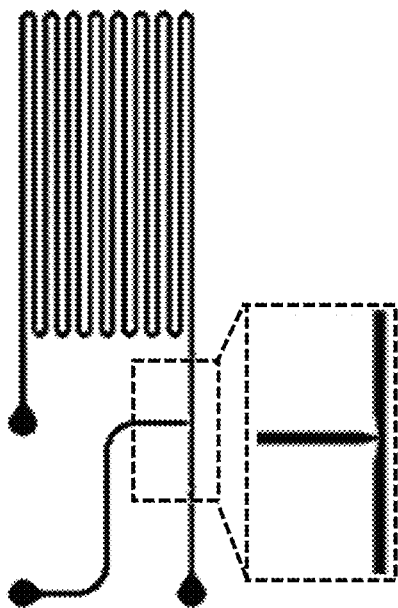
FIG. 15B is a schematic diagram illustrating a microchannel reactor, according to an embodiment herein.

The microchannel reactor 190 is experimentally tested with non-polar organic solvents. With respect to the gas-to-liquid TBP collector 40, the elute of sensor system includes solvents. The reactant with fluorescence substrate is, however, a water-based solution. Thus, droplet generating microfluidics is introduced. As indicated in FIG. 15A, various solvents are experimentally considered in terms of conservation of enzyme in the microchannel reactor 190 activity as denoted by the relative fluorophore intensity. Hexane is experimentally determined to be an appropriate solvent for both the gas-to-liquid TPB collector 40 and the microchannel reactor 190. The drop-wise addition channel 220 may also be embedded in the microchannel reactor 190. FIG. 15B shows an experimental configuration of the microchannel reactor 190. Continuous flow reaction was conducted using the microchannel reactor 190 prepared with the optimum conditions of an enzyme immobilization and organic solvent/water hybrid flow system. As a result, the fluorescence is observed from a cuvette 209 (denoted in FIG. 16A) in which the fluorescence substrate is connected with the product of the enzyme reaction to generate fluorescence luminescence. The fluorescence is observed at ~600 nm wavelength, excited at 550 nm wavelength. In the test of the sensing system, an inhibition substrate (e.g., TBP) is used at each concentration. Reactant flow rate also affects the inhibition, and the flow rate is determined to be ~50 µL/min. As the inhibitor solubilized flow passes into the microchannel reactor 190, the fluorescent intensity is observed to decrease. The competitive inhibition of TBP is direct, and the signal of fluorescence changes instantly.

Figure 16A:
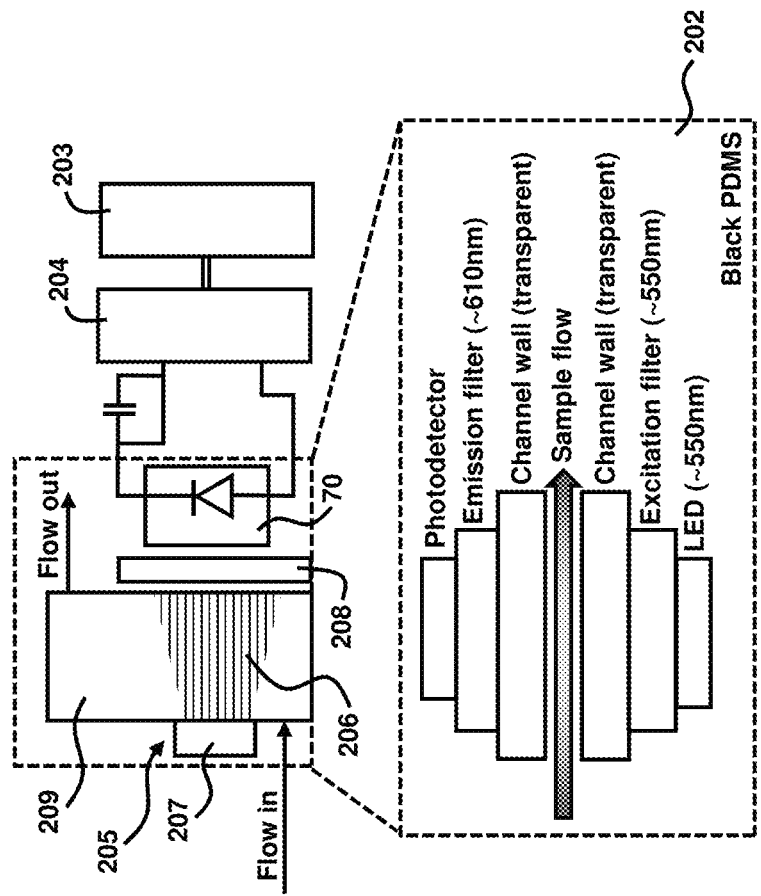
FIG. 16A is a schematic diagram illustrating a detector system, according to an embodiment herein.

The schematic configuration of the detector 70 is shown in FIG. 16A. Various geometries may be considered for effective detection of fluorescence emission in the microchannel reactor 190 and structures for direct lighting-detecting are determined. For fast detection of signal, the detector 70 size should be miniaturized to allow integration with the micro-fluidic chamber 50. For example, millimeter-sized components are used. An excitation light source 205 to generate light 206 may comprise an LED 207 and a polarizing filter 208. A cuvette 209 is positioned in the pathway of the light 206. Green filters may be used to reject stray light and excitation light. As emission wavelengths from the microchannel reactor 190, 570 nm, 590 nm, and 610 nm polarizing filters which reject each wavelength are tested, and the photodetector 70 is placed behind polarizing the filters 208 and are selected with suitable properties.

With respect to the data acquisition process, the current from the photodetector 70 is measured using a digital multi-meter (DMM) 204. As the system is operated, the detector 70 determines the fluorescence intensity associated with continuous reactant flow. The continuous changes in current are recorded and stored in a computer 203. The noise from the recorded data may be removed by adjusting a low pass digital filter as part of the data processing.

Figure 16B:
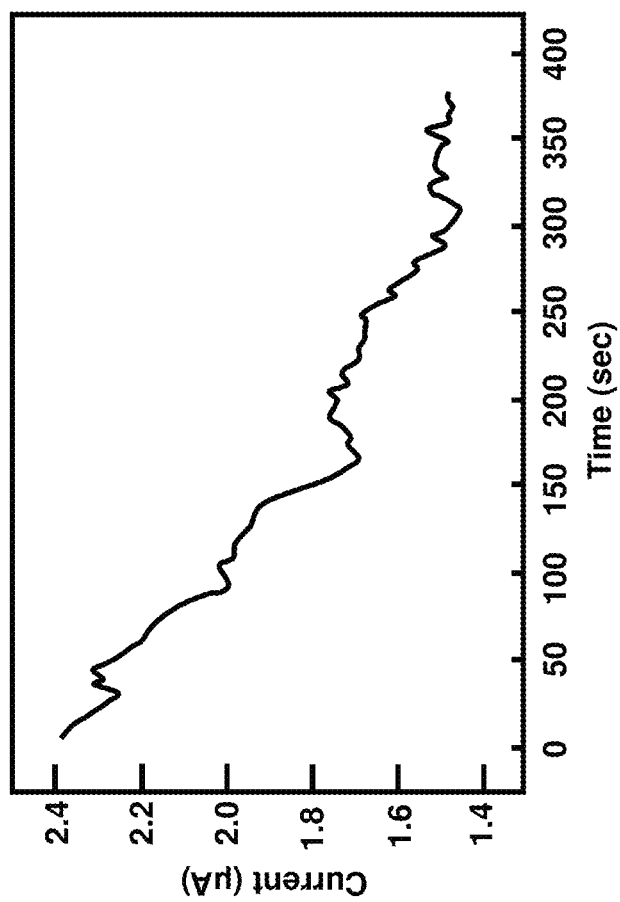
FIG. 16B is a graphical representation that correlates the current (corresponding to the fluorescence) as a function of time, according to an embodiment herein.

The fluorescence intensity is detected after emission of the light. The detector 70 mechanism is based on a fluorescence microscope. Green LEDs (550 nm) are selected and tested as excitation light sources with small sizes and strong output intensity. The photodetectors 70 should be sensitive at near red color light. The Polarizing filter 208 rejects all wavelengths below the emission wavelength. 570 nm and 590 nm filters are experimentally tested, and a high quality of wavelength rejection is realized with a 610 nm polarizing filter 208. Emission of the fluorescence substrate is known to be 600 nm, but a small size of the detected signal creates challenges in eliminating effects of light scattering penetration of excitation light 206 through the polarizing filter 208. Therefore, over 600 nm filters can be utilized. As the results of using a 610 nm filter 208, a small portion of fluorescence emission is rejected but the fluorescence information is more clea, and robust. Based on these efforts, all components were assembled with poly(methyl methacrylate) (PMMA). A two-dimensional laser cut PMMA pieces are bonded with epoxy, and a black PDMS 202 is used to cover the surrounding detector 70 to prevent light penetration from outside. Also, an aluminum channel is tested. The design of both the PMMA and aluminum detection channels are determined after optimization of various geometries of the positions of the excitation light source 205 and photodetector 70. When the detector 70 is prepared and integrated with the microchannel reactor 190, fluorescence intensity can be monitored and captured with a computer 203. The fluorescence information is collected by the detector 70, and the photodetector portion of the detector 70 generates current as the fluorescence intensity in the microfluidics. FIG. 16B summarizes the results. Time 0 is the starting point of inhibition and at ~200 pM TBP, the fluorescence changes as shown in FIG. 16B. The current scale is around nA before optimization. FIG. 16B shows results at the µA scale, which is significantly improved in terms of sensitivity and stability for actual use.

The developed sensing-detecting system should be integrated with the TBP collector 40. The experimental organo-phosphate detection system was designed and tested at the bread board level. The normal state of the system shows normal reaction conditions in which the chain reaction is performed. The chain reaction leads to the production of hydrogen which activates the fluorescence substrate (FIG. 13). The system shows fluorescence intensity corresponding to acetylcholine concentration, and the fluorescence intensity is affected by acetylcholine concentration and AChE activity. The system has continuous flow while it is operated. During flow operation, there is a constant amount of acetylcholine (10 mM) and fluorescence substrate (50 µl/mL). Thus, AChE activity affects the fluorescence intensity and if there is a strong inhibitor in the elute, AChE activity will be decreased. The normal state of the system, therefore, should show constant intensity of fluorescence. The alternating flow of hexane and reactant by the droplet generator for merging two flows is read out by the fluorescence detector 70 in FIG. 16A. Experimentally, a strong pink color indicated that the enzyme chain reactions are in the stationary phase. The TPB collector 40 is operated and TBP in the air could be collected and resolved into hexane. The system is a batch type and the TBP could be recovered by hexane flushing by two syringes. When the syringe with collected TBP is injected into the system, the reaction is inhibited.

Figure 17:
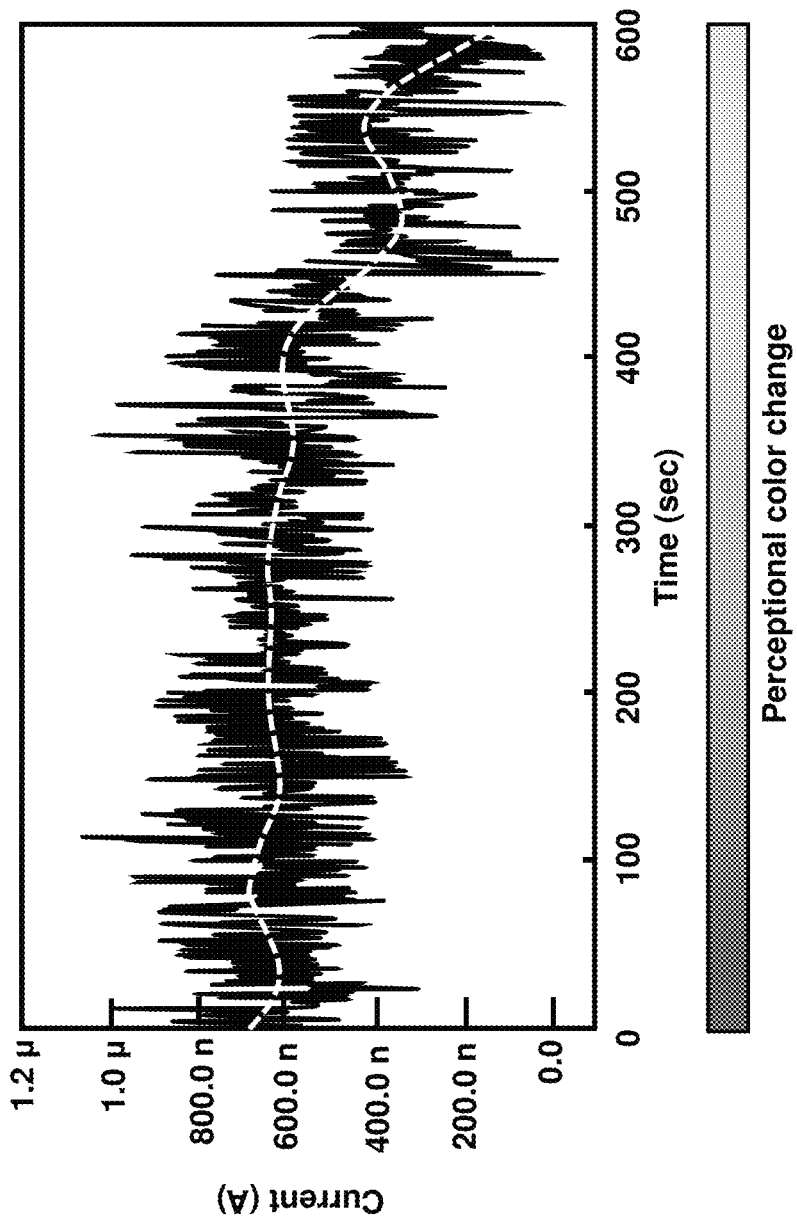
FIG. 17 is another graphical representation that correlates the current (corresponding to the fluorescence) as a function of time, according to an embodiment herein.

FIG. 17 shows the results of all experimental system operations. The fluorescence detector 70 generates current as there is over 610 nm light in the detector channel, and the signal data is the current value. The reaction system was stationary phase by ~400 sec. The constant fluorescence intensity reflects normal enzymatic activity. After 400 sec, as the TBP syringe is injected, the signal decreases which means that inhibition of AChE occurs by the TBP collected from air. The dashed adjoint line in FIG. 17 is filtered data which results from low pass filter adjustment. The decreased rate can be calculated to derive TBP concentration. With different amounts of organo-phosphates, the level of decreasing rate will be different. A high amount of organo-phosphate would lead to a more rapid decrease in fluorescence intensity. The calibration of decrease rate should be conducted for practical use. It is noted that enzyme activity can deactivate naturally as it is used. The deactivation without the presence of organo-phosphates should be addressed to yield stable operation in practical conditions. The effect is expected not to be significant, and it would be a slight change of the intensity. Therefore, the system should have a reference reactor which only has the flow of the reactant and fluorescence substrate. The reference reactor would improve the sensitivity and reliability of the system. Also, an automated data processing system could be developed for practical use in situ.

Figure 18:
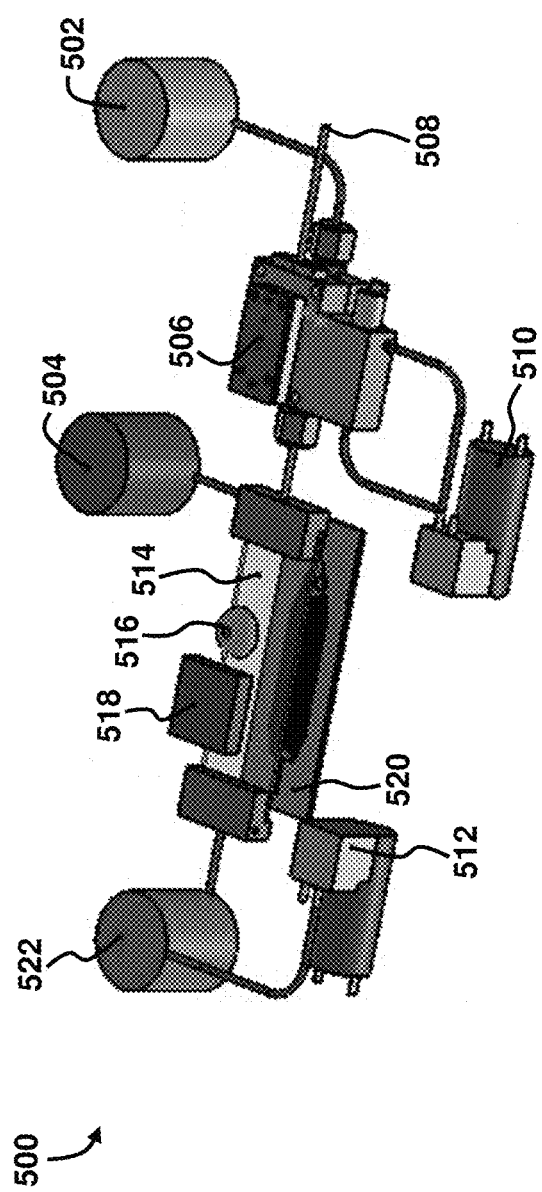
FIG. 18 is a schematic diagram illustrating a gas-phase analyte to liquid-phase transfer system, according to an embodiment herein.
Figure 19:
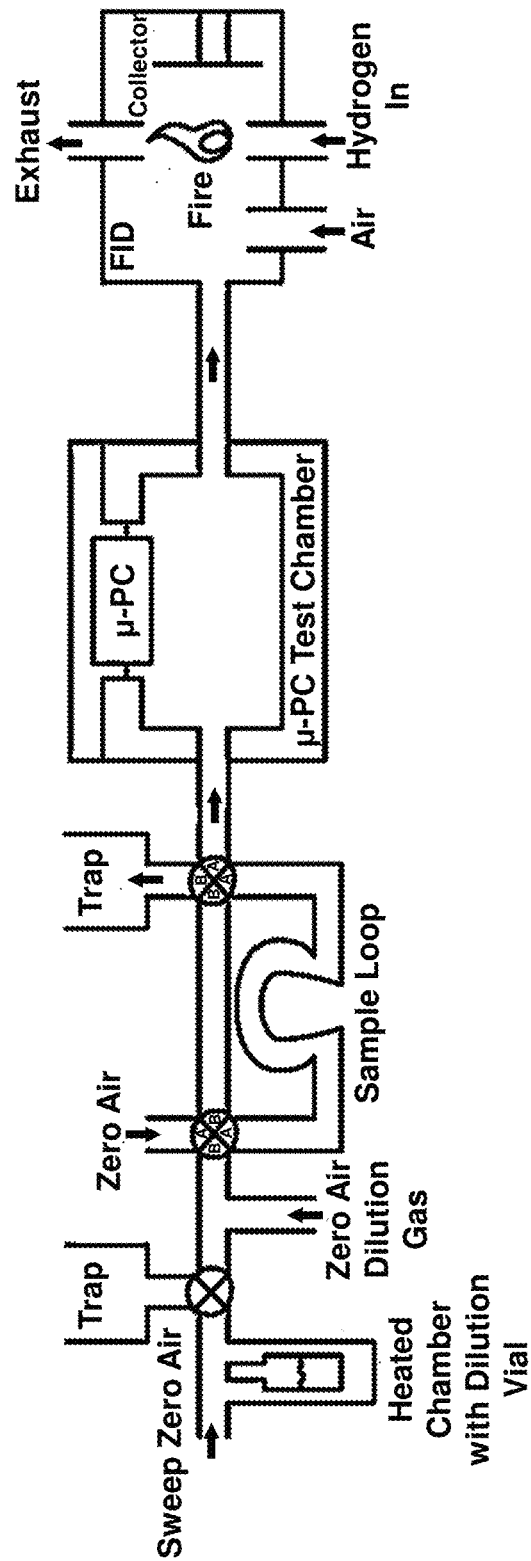
FIG. 19 is a schematic diagram illustrating a vapor generation and sample delivery system for characterizing a gas sample collector using a diffusion vial and sample loop, according to an embodiment herein.

An exemplary TBP detection system 500 that was experimentally tested is illustrated in FIG. 18. Generally, the system 500 comprises an AChE reservoir 502 operatively connected to an air-to-liquid micro-preconcentrator (μ-PC) 506. An air sample inlet 508 inputs into the μ-PC 506 also. An air sample vacuum pump 510 is operatively connected to the μ-PC 506. A microchannel reactor substrate 520 is operatively connected to the μ-PC 506. The microchannel reactor 520 comprises a transparent substrate cover 514, a LED light source 516, and a charge-coupled device (CCD) 518 as a photodiode for sensing emitted light. An enzyme reservoir 504 and waste reservoir 522 are operatively connected to the microchannel reactor substrate 520. A vacuum pump 512 for AChE transfer is operatively connected to the waste reservoir 522. A low-concentration mix of TBP in air passes over the μ-PC 506 where TBP is collected. The μ-PC 506 rapidly heats to develop a concentrated pulse of TBP vapor in a small chamber that encloses the μ-PC 506. A portion of the concentrated pulse accumulates in solvent on the opposite side of a membrane that forms one wall of the chamber. The elevated concentration and temperature enhance the transfer of TBP into solvent. Solvent with the collected TBP is transferred to the detector, where it is incubated with an immobilized acetylcholine esterase within a microchannel reactor 520. Aqueous solution for detection of acetylcholine esterase activity then passes over the immobilized enzyme, triggering a reaction producing a fluorescent substrate only if acetylcholine esterase is present and uninhibited by organophosphates/nerve agents. The LED light source 516 at 550 nm excites the fluorophore, and the emission is measured at 600 nm on a photodiode (CCD) 518. The percent reduction of fluorescence correlates with the concentration of TBP in the sample.

Hexane is brought into direct contact with the xerogel in the μ-PC 506 material. A pair of valves may be used to direct air and liquid flows during the sample collection cycle and the flush cycle where TBP is transferred to hexane. Between collection cycles, the μ-PC 506 material is heated and dried with air.

TBP is placed in a diffusion vial and set in a heated chamber with continuous 100 mL/min flow of zero air. The flux rate from the vial is determined gravimetrically by weekly weight measurements. With a D size diffusion vial with a 1-inch stem at ~80° C., the flux rate is determined to be 317 ng/min. This correlates with the estimated 390-ng/min flux rate for this vial. Since the sweep gas is 100 mL/min, the maximum concentration that can be delivered is approximately 400 ppb. The system 500 has a 500-μL sample loop so 2-ng of sample can be delivered to the test chamber shown in FIG. 19. Sample loops of 100 μL and 10 μL can also be used, and the sample stream could also be diluted to deliver lower concentrations of TBP samples.

The vapor system 500 was used to test some of the air-to-liquid sample collector concepts, but testing was also conducted with headspace samples of TBP in an open container. To estimate the concentration in headspace air samples, the upper limit can be determined by comparing the vapor pressure of TBP at ambient temperatures to the ambient pressure. At 25° C. the vapor pressure of TBP is on the order of 0.00113-mmHg. During testing, the barometric pressure is nominally 640-mmHg, so the concentration in the headspace is approximately 1.8-ppm. However, the concentration could be at least an order of magnitude lower as indicated in Skene, W., et al. "Vapor Pressure of Tri-n-Butyl Phosphonate," J. Chem. Eng., Data, 1995, 40, pp. 394-397, the complete disclosure of which, in its entirety, is herein incorporated by reference. Sampling headspace requires the dense vapor to travel up a container from the liquid surface and mix with the air. As a dense vapor, TBP would require a long equilibration time. Therefore, in working with headspace samples of TBP in air, it is estimated that the concentration is between 100 ppb and 1 ppm by volume.

Figure 20:
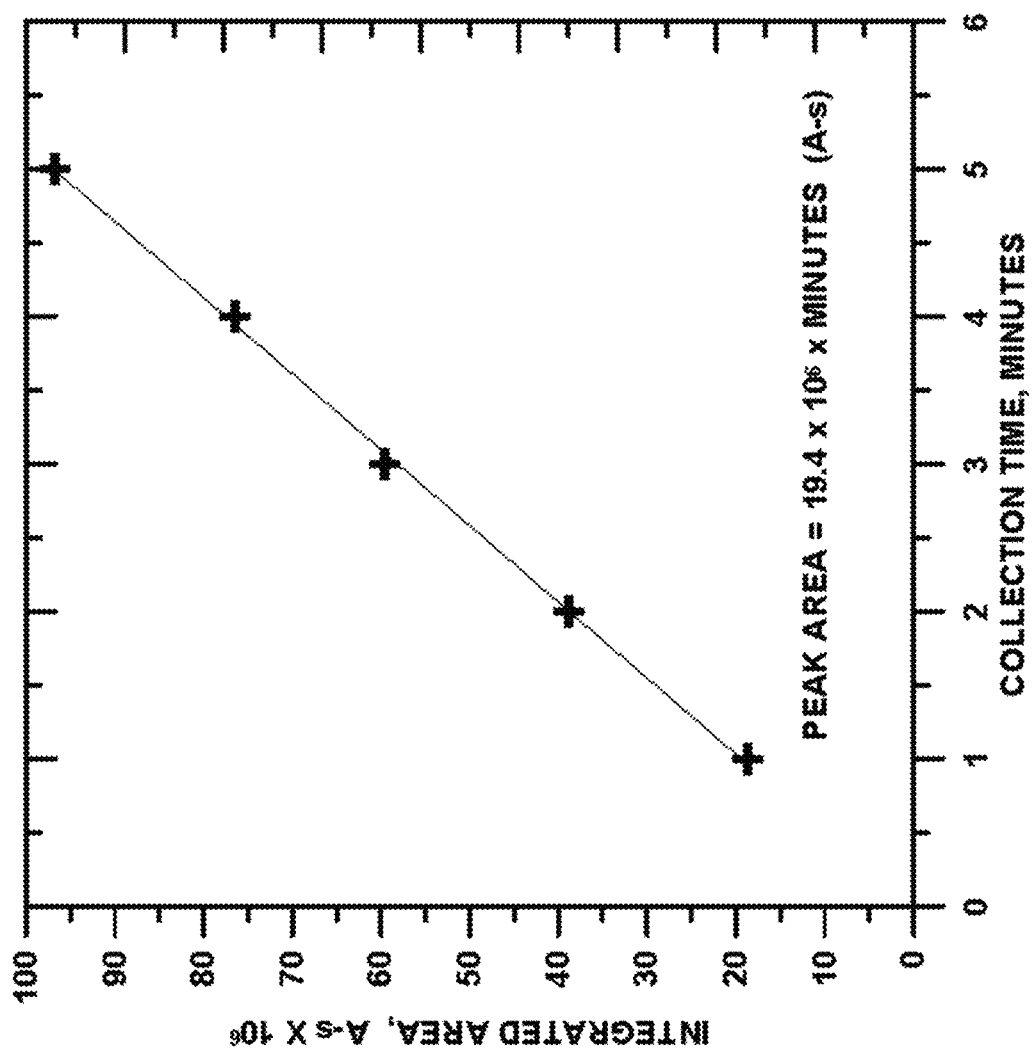
FIG. 20 is a graphical representation that correlates the integrated area NPD signal from PC-released TBP as a function of collection time, according to an embodiment herein.
Figure 21:
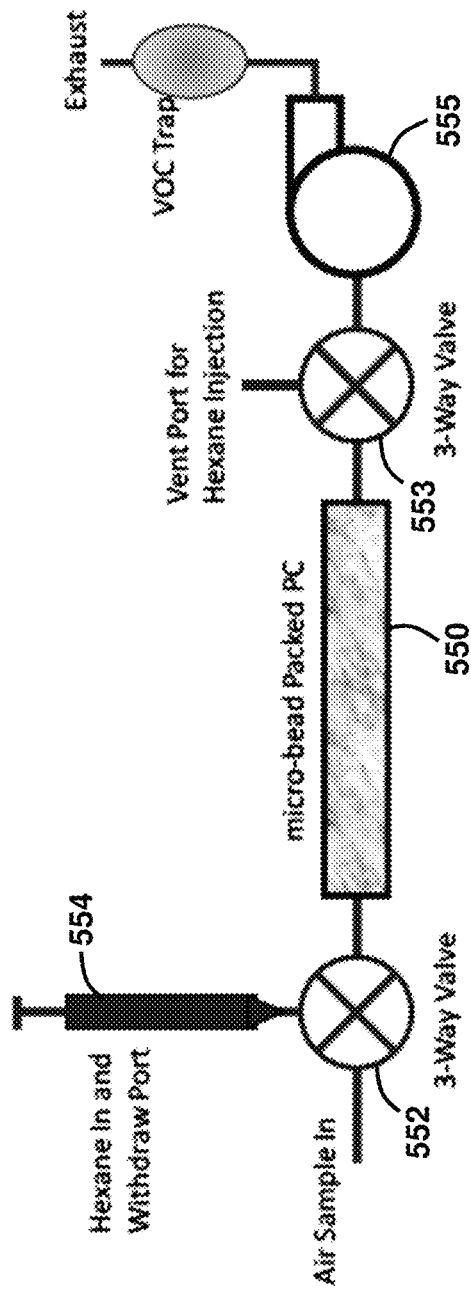
FIG. 21 is a schematic diagram illustrating a gas-to-liquid transfer system, according to an embodiment herein.

The roll of the μ-PC 506 in the system 500 is to capture the TBP in the air and concentrate it for delivery to the liquid. A series of tests were conducted to quantify the TBP capture and release properties for the μ-PC 506. The high-surface area μ-PC 506 is first exposed to the TPB stream and then the valve is switched to connect the μ-PC 506 to a nitrogen phosphorous detector (NPD). Voltage is applied to a heater on the μ-PC 506 to produce a concentrated plume on analyte on the NPD. FIG. 20 shows that the integrated area NPD signal trace is proportional to the mass of TBP that flows to the detector. The mass collected is proportional to the collection time, at least up to 5 minutes. Further testing shows that the linearity falters at long collection times. At 15 minutes, the measured total peak area is about 75% of the linear predicted area.

The ability of the μ-PC 506 to retain a sample of TBP is also tested. Even with warm nitrogen blowing over the surface of the μ-PC 506 for 4 extra minutes, there is no apparent loss in captured TBP. Certainly, longer intervals and higher flushing volumes will remove the TBP, but the xerogel coating has a high affinity for TBP to prevent quick loss in the captured TBP.

To estimate concentration capabilities of the μ-PC 506, the system is calibrated with a 500-μL sampling loop. This loop replaces the μ-PC 506 to introduce a known quantity of analyte to the NPD. The TBP sample is generated with a D-sized diffusion vial in an oven at 80° C. The flux rate of TBP is estimated to be 393 ng/min. The flow rate of the zero-air sweep gas through the diffusion vial chamber is measured with a bubble meter to be 55.1 mL/min. Based on these measurements, the concentration of TBP in the stream is 7.16 ng/mL, so a 500-μL sample loop would contain 3.58 ng of TBP.

Experimentally, it was determined that hexane could be flushed directly over the μ-PC 506 to remove concentrated TBP. An experimental apparatus shown in FIG. 21 was developed where the preconcentrator is a bed of microbeads 550 that are coated with xerogel. The microbeads 550 are packed in a tube that is wrapped with a heater for drying the packed bed after the hexane extraction. Valves 552, 553 at each end of the tube isolate the air collection system from the hexane.

During the TBP collection cycle, the valves 552, 553 are energized and a pump 555 pulls TBP-contaminated air through the microbeads 550. After collecting for a set amount of time, typically 10's of minutes, the pump 555 is switched off and the valves 552, 553 are de-energized. Hexane is introduced into the upstream side of the microbeads 550 using a 1-mL syringe 554. The hexane is then withdrawn through the same port and transferred to a detector system. A second syringe of clean hexane is flushed in and out of the collection tube to remove TBP remaining on the microbeads 550. The valves 552, 553 are then switched on, and the pump 555 and heaters are also switched on. The PC tube is heated to 60° C. to vaporize any remaining hexane. At this temperature, all hexane is removed in less than five minutes.

Figure 22:
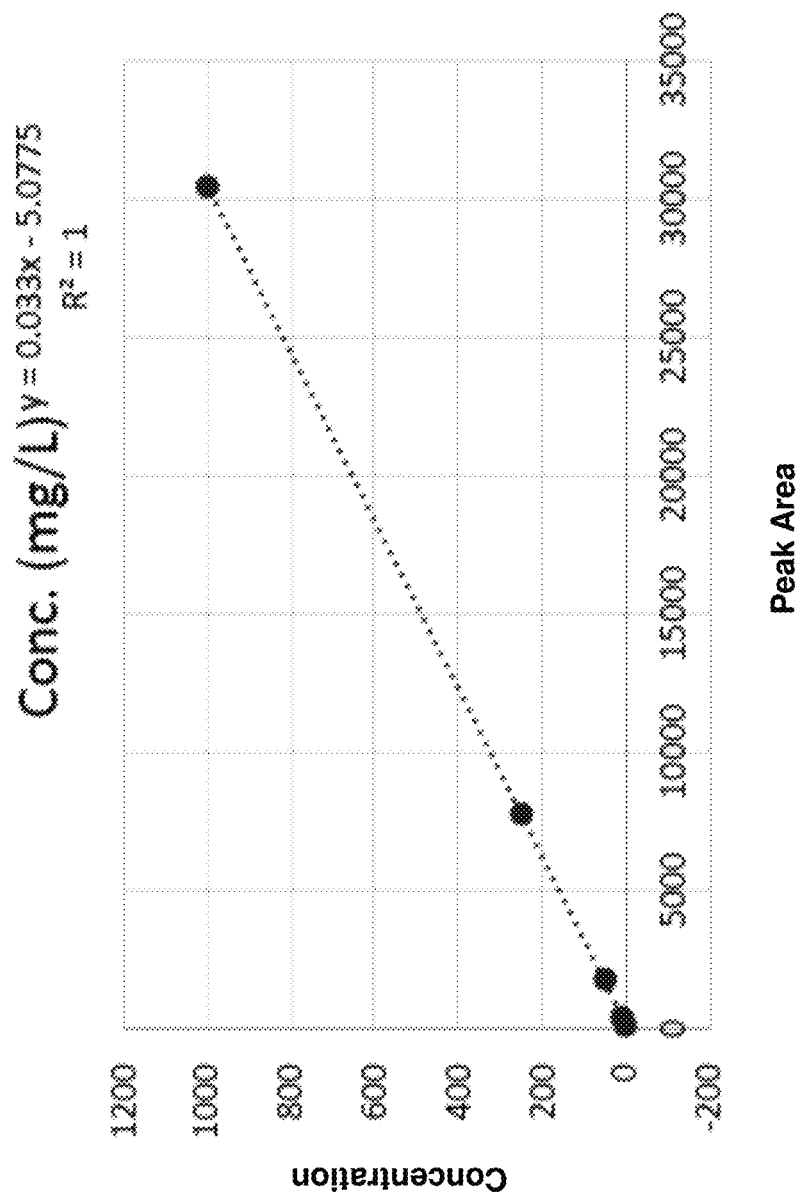
FIG. 22 is a graphical representation that correlates the concentration of TBP in hexane as a function of peak area, according to an embodiment herein.

The micro-bead packed PC system is tested to determine the concentration of TBP in the solvent. The original calibration is performed with acetonitrile, but the calibration is repeated with the hexane solvent and NPD. Five concentrations are run from 2 TBP/Liter hexane to 1000 µg/L, and the correlation between the area of the TBP peak and the concentration is shown in FIG. 22.

Tests were performed where TBP in air was drawn into the collector from the headspace above the surface of liquid TBP. After a collection of 25 minutes, 1 mL of hexane is injected into the µ-PC 506 and withdrawn from the same port. When 1-µL of this sample is injected into the calibrated flame ionization detector (FID), the peak area corresponds to 4.8 ng of TBP in the sample. A second flush 1-mL of hexane in the µ-PC 506 shows that the concentration goes to 8.4 ng of TBP, but a third flush of hexane shows that the µ-PC 506 is clean. Similar tests are performed at 5 and 10-minute collect times.

Figure 23:
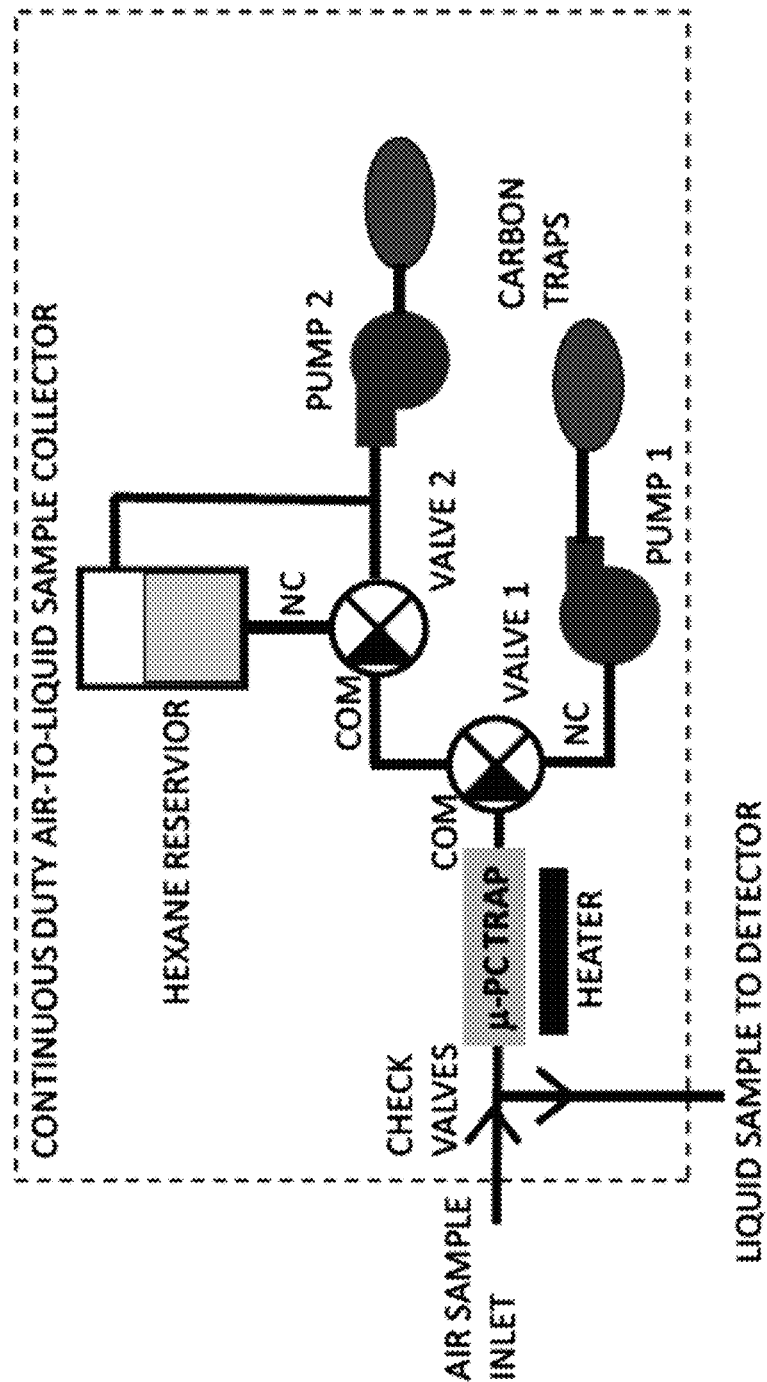
FIG. 23 is a schematic diagram illustrating a system for continuous operation of an air-to-liquid sampler, according to an embodiment herein.

FIG. 23 illustrates one exemplary approach for automating the collector and detector in the system. In this system shown in FIG. 23, pump 1 and valve 1 are energized to pull an air sample into the collector. Check valves at the inlet of the µ-PC trap only allows the flow to come from one port of a tee at the inlet. After the collection, pump 2 and valve 2 energize to flush hexane back through the µ-PC trap. A check valve at the inlet tee directs the flow to the detector system. After a couple of trap volumes of hexane is flushed through the µ-PC, valve 2 de-energizes, and air pushes remaining hexane out of the trap. Additionally, pump 1, valve 1, and the heater can be activated to dry the trap before the next collection cycle.

Accordingly, the experiments demonstrate an organophosphates detection system based on an inhibition mechanism for acetylcholinesterase. A microchannel reactor 190 with chain reaction to yield fluorescence is experimentally demonstrated and a detection sub-system is constructed to readout the fluorescence intensity. The gas-to-liquid TBP collector 40 gathers TBP in the air, and transfers it to the liquid (hexane), which is injected into the enzymatic reaction microchannel reactor 190. The detector 70 allows sensing of changes in the reaction rate by measuring the inverse proportionality to organo-phosphate concentration to fluorescence.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Those skilled in the art will recognize that the embodiments herein can be practiced with modification within the spirit and scope of the appended claims.

What is claimed is:

1. A system comprising:
    a gas-to-liquid collector configured to transfer a vapor by autonomous liquid extraction to a mobile organic liquid phase, the vapor comprising an organo-phosphate;
    a micro-fluidic chamber, configured to receive the mobile organic liquid phase from the gas-to-liquid collector, the micro-fluidic chamber comprising enzymes therein that are configured to react with a reagent to yield a hydrogen ion and an electron, the enzymes comprising acetylcholine esterase, cyclooxygenase, horseradish peroxidase, or combinations thereof;
    a substrate configured to receive the mobile organic liquid phase with the hydrogen ion and the electron from the micro-fluidic chamber, the substrate configured to chemically react with the hydrogen ion and the electron to yield a fluorophore; and
    a detector configured to detect and to perform real-time analysis of fluorescence of the fluorophore,
    wherein presence of the organo-phosphate inhibits the enzymes within the micro-fluidic chamber, thereby reducing a yield of the fluorophore, and wherein a decrease in fluorescence corresponds to an increase in organo-phosphate.

2. The system of claim 1, wherein the gas-to-liquid collector comprises a tube comprising silica gel coated with a xerogel to collect the target analyte.

3. The system of claim 1, wherein the gas-to-liquid collector comprises a microelectromechanical systems (MEMS) device to collect the organo-phosphate.

4. The system of claim 1, comprising:
    a reservoir configured to store the mobile organic liquid phase; and
    a valve configured to control delivery of the mobile organic liquid phase from the reservoir to the gas-to-liquid collector.

5. The system of claim 1, further comprising:
    an alarm that is triggered upon detection of the organo-phosphate at a concentration that is greater than a predetermined level.

6. The system of claim 1, wherein the mobile organic liquid phase comprises a non-polar solvent.

7. The system of claim 6, wherein the non-polar solvent comprises hexane.

8. The system of claim 1, wherein the micro-fluidic chamber includes an inner surface and the enzymes are immobilized to the inner surface of micro-fluidic chamber.

9. The system of claim 8, wherein the enzymes are immobilized by a cross-linker.

* * * * *